US010921886B2

(12) United States Patent
Connor

(10) Patent No.: US 10,921,886 B2
(45) Date of Patent: Feb. 16, 2021

(54) CIRCUMFERENTIAL ARRAY OF ELECTROMYOGRAPHIC (EMG) SENSORS

(71) Applicant: Robert A. Connor, Burnsville, MN (US)

(72) Inventor: Robert A. Connor, Burnsville, MN (US)

(73) Assignee: Medibotics LLC, St. Paul, MN (US)

( * ) Notice: Subject to any disclaimer, the term of this patent is extended or adjusted under 35 U.S.C. 154(b) by 312 days.

(21) Appl. No.: 16/017,439

(22) Filed: Jun. 25, 2018

(65) Prior Publication Data
US 2018/0307314 A1 Oct. 25, 2018

Related U.S. Application Data

(63) Continuation-in-part of application No. 16/010,448, filed on Jun. 16, 2018, now Pat. No. 10,602,965, which is a continuation-in-part of application No. 15/702,081, filed on Sep. 12, 2017, now Pat. No. 10,716,510, which is a continuation-in-part of application No. 15/227,254, filed on Aug. 3, 2016, now Pat. No. 10,321,873, which is a continuation-in-part of application No. 15/130,995, filed on Apr. 17, 2016, now Pat. No. 9,891,718, said
(Continued)

(51) Int. Cl.
| | | |
|---|---|---|
| *A61B 5/00* | (2006.01) | |
| *G06F 3/01* | (2006.01) | |
| *A61B 5/0488* | (2006.01) | |
| *G01R 27/02* | (2006.01) | |
| *A61B 5/0492* | (2006.01) | |
| *A61B 5/11* | (2006.01) | |
| *G01R 29/08* | (2006.01) | |

(52) U.S. Cl.
CPC ............ *G06F 3/015* (2013.01); *A61B 5/0488* (2013.01); *A61B 5/0492* (2013.01); *A61B 5/1123* (2013.01); *G01R 27/02* (2013.01); *G01R 29/0814* (2013.01); *G01R 29/0878* (2013.01); *G06F 3/017* (2013.01); *A61B 5/681* (2013.01); *A61B 5/6804* (2013.01); *A61B 5/6824* (2013.01); *A61B 5/6826* (2013.01); *A61B 5/6828* (2013.01); *A61B 5/6829* (2013.01); *A61B 2562/046* (2013.01)

(58) Field of Classification Search
CPC ... A61B 5/0488; A61B 5/0492; A61B 5/1123; G06F 3/015; G06F 3/017; G01R 27/02; G01R 29/0814; G01R 29/0878
USPC .......................................................... 600/547
See application file for complete search history.

(56) References Cited

U.S. PATENT DOCUMENTS

| | | | |
|---|---|---|---|
| 5,474,083 A | 12/1995 | Church et al. | |
| 6,443,906 B1 * | 9/2002 | Ting ...................... | A61B 5/681 600/490 |

(Continued)

*Primary Examiner* — Max F Hindenburg

(57) ABSTRACT

This invention is a wearable circumferential array of electromyographic (EMG) sensors with a plurality of rings and columns of sensors which collect electromagnetic energy data concerning neuromuscular activity and functions as a Human-to-Computer Interface (HCI). In an example, it can be incorporated into a wearable device or clothing accessory such as an arm band, wrist band, finger ring, leg band, ankle band, bracelet, or watch strap. In an example, it can be incorporated into the cuff or sleeve of an article of clothing such as a shirt or a pair of shorts.

17 Claims, 3 Drawing Sheets

Related U.S. Application Data application No. 15/227,254 is a continuation-in-part of application No. 15/079,447, filed on Mar. 24, 2016, now Pat. No. 10,234,934, which is a continuation-in-part of application No. 14/463,741, filed on Aug. 20, 2014, now Pat. No. 9,588,582, said application No. 15/079,447 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, said application No. 15/227,254 is a continuation-in-part of application No. 14/736,652, filed on Jun. 11, 2015, now abandoned, which is a continuation-in-part of application No. 14/664,832, filed on Mar. 21, 2015, now Pat. No. 9,582,072, said application No. 15/227,254 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, said application No. 15/702,081 is a continuation-in-part of application No. 14/795,373, filed on Jul. 9, 2015, now abandoned, which is a continuation-in-part of application No. 14/736,652, filed on Jun. 11, 2015, now abandoned, which is a continuation-in-part of application No. 14/664,832, filed on Mar. 21, 2015, now Pat. No. 9,582,072, said application No. 16/010,448 is a continuation-in-part of application No. 15/227,254, filed on Aug. 3, 2016, now Pat. No. 10,321,873, which is a continuation-in-part of application No. 15/130,995, filed on Apr. 17, 2016, now Pat. No. 9,891,718, said application No. 15/227,254 is a continuation-in-part of application No. 15/079,447, filed on Mar. 24, 2016, now Pat. No. 10,234,934, which is a continuation-in-part of application No. 14/463,741, filed on Aug. 20, 2014, now Pat. No. 9,588,582, said application No. 15/079,447 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, said application No. 15/227,254 is a continuation-in-part of application No. 14/736,652, filed on Jun. 11, 2015, now abandoned, which is a continuation-in-part of application No. 14/664,832, filed on Mar. 21, 2015, now Pat. No. 9,582,072, said application No. 15/227,254 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, application No. 16/017,439, which is a continuation-in-part of application No. 15/725,330, filed on Oct. 5, 2017, now Pat. No. 10,607,507, which is a continuation-in-part of application No. 15/431,769, filed on Feb. 14, 2017, which is a continuation-in-part of application No. 14/330,649, filed on Jul. 14, 2014, now abandoned, which is a continuation-in-part of application No. 13/523,739, filed on Jun. 14, 2012, now Pat. No. 9,042,596, and a continuation-in-part of application No. 13/797,955, filed on Mar. 12, 2013, now Pat. No. 9,456,916, said application No. 15/431,769 is a continuation-in-part of application No. 14/992,073, filed on Jan. 11, 2016, now abandoned, which is a continuation-in-part of application No. 14/599,522, filed on Jan. 18, 2015, now Pat. No. 9,814,426, which is a continuation-in-part of application No. 14/562,719, filed on Dec. 7, 2014, now Pat. No. 10,130,277, said application No. 14/992,073 is a continuation-in-part of application No. 14/550,953, filed on Nov. 22, 2014, now abandoned, and a continuation-in-part of application No. 13/616,238, filed on Sep. 14, 2012, now abandoned, said application No. 15/431,769 is a continuation-in-part of application No. 15/206,215, filed on Jul. 8, 2016, now abandoned, which is a continuation-in-part of application No. 14/948,308, filed on Nov. 21, 2015, now abandoned, which is a continuation-in-part of application No. 13/901,099, filed on May 23, 2013, now Pat. No. 9,254,099, and a continuation-in-part of application No. 14/132,292, filed on Dec. 18, 2013, now Pat. No. 9,442,100, and a continuation-in-part of application No. 14/449,387, filed on Aug. 1, 2014, now abandoned, said application No. 15/206,215 is a continuation-in-part of application No. 14/951,475, filed on Nov. 24, 2015, now Pat. No. 10,314,492, which is a continuation-in-part of application No. 13/901,131, filed on May 23, 2013, now Pat. No. 9,536,449, and a continuation-in-part of application No. 14/071,112, filed on Nov. 4, 2013, now abandoned, and a continuation-in-part of application No. 14/623,337, filed on Feb. 16, 2015, now Pat. No. 9,582,035, said application No. 15/431,769 is a continuation-in-part of application No. 15/236,401, filed on Aug. 13, 2016, now abandoned, which is a continuation-in-part of application No. 15/136,948, filed on Apr. 24, 2016, now Pat. No. 10,234,942, which is a continuation of application No. 14/599,522, filed on Jan. 18, 2015, now Pat. No. 9,814,426, said application No. 15/236,401 is a continuation-in-part of application No. 14/599,522, filed on Jan. 18, 2015, now Pat. No. 9,814,426, said application No. 15/431,769 is a continuation-in-part of application No. 15/294,746, filed on Oct. 16, 2016, now Pat. No. 10,627,861, which is a continuation-in-part of application No. 14/623,337, filed on Feb. 16, 2015, now Pat. No. 9,582,035, said application No. 15/294,746 is a continuation-in-part of application No. 14/951,475, filed on Nov. 24, 2015, now Pat. No. 10,314,492, said application No. 15/725,330 is a continuation-in-part of application No. 14/951,475, filed on Nov. 24, 2015, now Pat. No. 10,314,492, which is a continuation-in-part of application No. 13/901,131, filed on May 23, 2013, now Pat. No. 9,536,449, and a continuation-in-part of application No. 14/071,112, filed on Nov. 4, 2013, now abandoned, and a continuation-in-part of application No. 14/623,337, filed on Feb. 16, 2015, now Pat. No. 9,582,035, application No. 16/017,439, which is a continuation-in-part of application No. 14/795,373, filed on Jul. 9, 2015, now abandoned, which is a continuation-in-part of application No. 14/736,652, filed on Jun. 11, 2015, now abandoned, which is a continuation-in-part of application No. 14/664,832, filed on Mar. 21, 2015, now Pat. No. 9,582,072.

(60) Provisional application No. 62/538,793, filed on Jul. 30, 2017, provisional application No. 62/449,735, filed on Jan. 24, 2017, provisional application No. 62/357,957, filed on Jul. 2, 2016, provisional application No. 62/150,886, filed on Apr. 22, 2015, provisional application No. 61/878,893, filed on Sep. 17, 2013, provisional application No. 61/976,650, filed on Apr. 8, 2014, provisional application No. 62/014,747, filed on Jun. 20, 2014, provisional application No. 62/100,217, filed on Jan. 6, 2015, provisional application No. 62/065,032, filed on Oct. 17, 2014, provisional application No. 62/086,053, filed on Dec. 1, 2014, provisional application No. 62/182,473, filed on Jun. 20, 2015, provisional application No. 62/187,906, filed on Jul. 2, 2015, provisional application No. 62/538,793, filed on Jul. 30, 2017, provisional application No. 62/638,237, filed on Jun. 11, 2018, provisional application No. 61/729,494, filed on Nov. 23, 2012, provisional application No. 61/932,517, filed on Jan. 28, 2014, provisional application No. 61/939,244, filed on Feb. 12, 2014, provisional application No. 62/017,615, filed on Jun. 26, 2014, provisional application No. 62/089,696, filed on Dec. 9, 2014, provisional application No. 62/245,311, filed on Oct. 23, 2015, provisional application No. 62/349,277, filed on Jun. 13, 2016, provisional application No. 62/160,172, filed on May 12, 2015, provisional application No. 62/169,661, filed on Jun. 2, 2015, provisional application No. 62/303,126, filed on Mar. 3, 2016, provisional application No. 62/322,594, filed on Apr. 14, 2016, provisional application No. 61/944,090, filed on Feb. 25, 2014, provisional application No. 61/948,124, filed on Mar. 5, 2014, provisional application No. 62/106,856, filed on Jan. 23, 2015, provisional application No. 62/111,163, filed on Feb. 3, 2015, provisional application No. 62/113,423, filed on Feb. 7, 2015, provisional application No. 62/115,691, filed on Feb. 13, 2015, provisional application No. 62/311,462, filed on Mar. 22, 2016, provisional application No. 62/439,147, filed on Dec. 26, 2016, provisional application No. 62/549,587, filed on Aug. 24, 2017.

(56) References Cited

U.S. PATENT DOCUMENTS

| | | | |
|---|---|---|---|
| 7,152,470 B2 | 12/2006 | Impio et al. | |
| 7,559,902 B2 | 7/2009 | Ting et al. | |
| 7,747,303 B2 * | 6/2010 | Eichler | A61B 5/0536 600/390 |
| 7,878,030 B2 | 2/2011 | Burr | |
| 8,082,762 B2 | 12/2011 | Burr | |
| 8,162,857 B2 | 4/2012 | Lanfermann et al. | |
| 8,170,656 B2 | 5/2012 | Tan et al. | |
| 8,185,231 B2 | 5/2012 | Fernandez | |
| 8,945,328 B2 | 2/2015 | Longinotti-Buitoni et al. | |
| 8,948,839 B1 | 2/2015 | Longinotti-Buitoni et al. | |
| 8,998,831 B2 * | 4/2015 | Sankai | A61H 1/0288 601/40 |
| 9,037,530 B2 | 5/2015 | Tan et al. | |
| 9,039,613 B2 | 5/2015 | Kuck et al. | |
| 9,278,453 B2 * | 3/2016 | Assad | B25J 9/1694 |
| 9,392,951 B2 * | 7/2016 | Greenspan | A61B 5/042 |
| 9,675,298 B2 * | 6/2017 | Kim | A61B 5/7214 |
| 10,152,082 B2 * | 12/2018 | Bailey | G06F 1/163 |
| 2005/0054941 A1 | 3/2005 | Ting et al. | |
| 2009/0229039 A1 | 9/2009 | Kuck et al. | |
| 2009/0326406 A1 | 12/2009 | Tan et al. | |
| 2010/0036288 A1 | 2/2010 | Lanfermann et al. | |
| 2010/0041974 A1 | 2/2010 | Ting et al. | |
| 2011/0166491 A1 | 7/2011 | Sankai | |
| 2012/0188158 A1 | 7/2012 | Tan et al. | |
| 2013/0150697 A1 * | 6/2013 | Imai | A61B 5/11 600/384 |
| 2013/0211208 A1 | 8/2013 | Varadan et al. | |
| 2013/0317648 A1 | 11/2013 | Assad | |
| 2014/0070957 A1 | 3/2014 | Longinotti-Buitoni et al. | |
| 2014/0135593 A1 | 5/2014 | Jayalth et al. | |
| 2014/0142459 A1 | 5/2014 | Jayalth et al. | |
| 2014/0198034 A1 | 7/2014 | Bailey et al. | |
| 2014/0198035 A1 | 7/2014 | Bailey et al. | |
| 2014/0213929 A1 | 7/2014 | Dunbar | |
| 2014/0240103 A1 | 8/2014 | Lake et al. | |
| 2014/0240223 A1 | 8/2014 | Lake et al. | |
| 2014/0318699 A1 | 10/2014 | Longinotti-Buitoni et al. | |
| 2014/0334083 A1 | 11/2014 | Bailey | |
| 2014/0378812 A1 | 12/2014 | Saroka et al. | |
| 2015/0025355 A1 | 1/2015 | Bailey et al. | |
| 2015/0040282 A1 | 2/2015 | Longinotti-Buitoni et al. | |
| 2015/0045699 A1 | 2/2015 | Mokaya et al. | |
| 2015/0051470 A1 | 2/2015 | Bailey et al. | |
| 2015/0057506 A1 | 2/2015 | Luna et al. | |
| 2015/0057770 A1 | 2/2015 | Bailey et al. | |
| 2015/0065840 A1 | 3/2015 | Bailey | |
| 2015/0070270 A1 | 3/2015 | Bailey et al. | |
| 2015/0084860 A1 | 3/2015 | Aleem et al. | |
| 2015/0109202 A1 | 4/2015 | Ataee et al. | |
| 2015/0124566 A1 | 5/2015 | Lake et al. | |
| 2015/0141784 A1 | 5/2015 | Morun et al. | |
| 2015/0143601 A1 | 5/2015 | Longinotti-Buitoni et al. | |
| 2015/0148619 A1 | 5/2015 | Berg et al. | |
| 2015/0148641 A1 | 5/2015 | Morun et al. | |
| 2015/0169074 A1 | 6/2015 | Ataee et al. | |
| 2015/0297134 A1 * | 10/2015 | Albert | A61B 5/0205 600/384 |

* cited by examiner

CIRCUMFERENTIAL ARRAY OF ELECTROMYOGRAPHIC (EMG) SENSORS

CROSS-REFERENCE TO RELATED APPLICATIONS

This patent application:

(A) is a CIP (Continuation In Part) of ap. (application #) 16010448 filed on 2018 Jun. 16; ap. 16010448 is a CIP of ap. 15702081 filed on 2017 Sep. 12; ap. 15702081 claims the priority benefit of ap. 62538793 filed on 2017 Jul. 30; ap. 15702081 claims the priority benefit of ap. 62449735 filed on 2017 Jan. 24; ap. 15702081 is a CIP of ap. 15227254 filed on 2016 Aug. 3; ap. 15227254 claims the priority benefit of ap. 62357957 filed on 2016 Jul. 2; ap. 15227254 is a CIP of ap. 15130995 filed on 2016 Apr. 17; ap. 15130995 claims the priority benefit of ap. 62150886 filed on 2015 Apr. 22; ap. 15227254 is a CIP of ap. 15079447 filed on 2016 Mar. 24; ap. 15079447 is a CIP of ap. 14463741 filed on 2014 Aug. 20; ap. 14463741 claims the priority benefit of ap. 61878893 filed on 2013 Sep. 17; ap. 15079447 is a CIP of ap. 14664832 filed on 2015 Mar. 21; ap. 14664832 is a CIP of ap. 14463741 filed on 2014 Aug. 20; ap. 14463741 claims the priority benefit of ap. 61878893 filed on 2013 Sep. 17; ap. 14664832 claims the priority benefit of ap. 61976650 filed on 2014 Apr. 8; ap. 15079447 claims the priority benefit of ap. 62150886 filed on 2015 Apr. 22; ap. 15227254 is a CIP of ap. 14736652 filed on 2015 Jun. 11; ap. 14736652 is a CIP of ap. 14664832 filed on 2015 Mar. 21; ap. 14736652 claims the priority benefit of ap. 62014747 filed on 2014 Jun. 20; ap. 14736652 claims the priority benefit of ap. 62100217 filed on 2015 Jan. 6; ap. 15227254 is a CIP of ap. 14664832 filed on 2015 Mar. 21; ap. 14664832 is a CIP of ap. 14463741 filed on 2014 Aug. 20; ap. 14463741 claims the priority benefit of ap. 61878893 filed on 2013 Sep. 17; ap. 14664832 claims the priority benefit of ap. 61976650 filed on 2014 Apr. 8; ap. 15702081 is a CIP of ap. 14795373 filed on 2015 Jul. 9; ap. 14795373 is a CIP of ap. 14736652 filed on 2015 Jun. 11; ap. 14736652 is a CIP of ap. 14664832 filed on 2015 Mar. 21; ap. 14736652 claims the priority benefit of ap. 62014747 filed on 2014 Jun. 20; ap. 14736652 claims the priority benefit of ap. 62100217 filed on 2015 Jan. 6; ap. 14795373 claims the priority benefit of ap. 62065032 filed on 2014 Oct. 17; ap. 14795373 claims the priority benefit of ap. 62086053 filed on 2014 Dec. 1; ap. 14795373 claims the priority benefit of ap. 62182473 filed on 2015 Jun. 20; ap. 14795373 claims the priority benefit of ap. 62187906 filed on 2015 Jul. 2; ap. 16010448 claims the priority benefit of ap. 62538793 filed on 2017 Jul. 30; ap. 16010448 is a CIP of ap. 15227254 filed on 2016 Aug. 3; ap. 15227254 claims the priority benefit of ap. 62357957 filed on 2016 Jul. 2; ap. 15227254 is a CIP of ap. 15130995 filed on 2016 Apr. 17; ap. 15130995 claims the priority benefit of ap. 62150886 filed on 2015 Apr. 22; ap. 15227254 is a CIP of ap. 15079447 filed on 2016 Mar. 24; ap. 15079447 is a CIP of ap. 14463741 filed on 2014 Aug. 20; ap. 14463741 claims the priority benefit of ap. 61878893 filed on 2013 Sep. 17; ap. 15079447 is a CIP of ap. 14664832 filed on 2015 Mar. 21; ap. 14664832 is a CIP of ap. 14463741 filed on 2014 Aug. 20; ap. 14463741 claims the priority benefit of ap. 61878893 filed on 2013 Sep. 17; ap. 14664832 claims the priority benefit of ap. 61976650 filed on 2014 Apr. 8; ap. 15079447 claims the priority benefit of ap. 62150886 filed on 2015 Apr. 22; ap. 15227254 is a CIP of ap. 14736652 filed on 2015 Jun. 11; ap. 14736652 is a CIP of ap. 14664832 filed on 2015 Mar. 21; ap. 14736652 claims the priority benefit of ap. 62014747 filed on 2014 Jun. 20; ap. 14736652 claims the priority benefit of ap. 62100217 filed on 2015 Jan. 6; ap. 15227254 is a CIP of ap. 14664832 filed on 2015 Mar. 21; ap. 14664832 is a CIP of ap. 14463741 filed on 2014 Aug. 20; ap. 14463741 claims the priority benefit of ap. 61878893 filed on 2013 Sep. 17; ap. 14664832 claims the priority benefit of ap. 61976650 filed on 2014 Apr. 8; ap. 16010448 claims the priority benefit of ap. 62683237 filed on 2018 Jun. 11;

(B) is a CIP of ap. 15725330 filed on 2017 Oct. 5; ap. 15725330 is a CIP of ap. 15431769 filed on 2017 Feb. 13; ap. 15431769 is a CIP of ap. 14330649 filed on 2014 Jul. 14; ap. 14330649 is a CIP of ap. 13523739 filed on 2012 Jun. 14; ap. 14330649 is a CIP of ap. 13797955 filed on 2013 Mar. 12; ap. 13797955 claims the priority benefit of ap. 61729494 filed on 2012 Nov. 23; ap. 15431769 is a CIP of ap. 14992073 filed on 2016 Jan. 11; ap. 14992073 is a CIP of ap. 14599522 filed on 2015 Jan. 18; ap. 14599522 is a CIP of ap. 14562719 filed on 2014 Dec. 7; ap. 14562719 claims the priority benefit of ap. 61932517 filed on 2014 Jan. 28; ap. 14599522 claims the priority benefit of ap. 61932517 filed on 2014 Jan. 28; ap. 14599522 claims the priority benefit of ap. 61939244 filed on 2014 Feb. 12; ap. 14599522 claims the priority benefit of ap. 62017615 filed on 2014 Jun. 26; ap. 14599522 claims the priority benefit of ap. 62089696 filed on 2014 Dec. 6; ap. 14992073 is a CIP of ap. 14550953 filed on 2014 Nov. 22; ap. 14992073 is a CIP of ap. 13616238 filed on 2012 Sep. 14; ap. 15431769 is a CIP of ap. 15206215 filed on 2016 Jul. 8; ap. 15206215 is a CIP of ap. 14948308 filed on 2015 Nov. 21; ap. 14948308 is a CIP of ap. 13901099 filed on 2013 May 23; ap. 14948308 is a CIP of ap. 14132292 filed on 2013 Dec. 18; ap. 14948308 is a CIP of ap. 14449387 filed on 2014 Aug. 1; ap. 15206215 is a CIP of ap. 14951475 filed on 2015 Nov. 24; ap. 14951475 is a CIP of ap. 13901131 filed on 2013 May 23; ap. 14951475 is a CIP of ap. 14071112 filed on 2013 Nov. 4; ap. 14951475 is a CIP of ap. 14623337 filed on 2015 Feb. 16; ap. 14951475 claims the priority benefit of ap. 62245311 filed on 2015 Oct. 23; ap. 15206215 claims the priority benefit of ap. 62349277 filed on 2016 Jun. 13; ap. 15431769 is a CIP of ap. 15236401 filed on 2016 Aug. 13; ap. 15236401 is a CIP of ap. 15136948 filed on 2016 Apr. 24; ap. 15136948 is a CIP of ap. 14599522 filed on 2015 Jan. 18; ap. 15136948 claims the priority benefit of ap. 61932517 filed on 2014 Jan. 28; ap. 15136948 claims the priority benefit of ap. 61939244 filed on 2014 Feb. 12; ap. 15136948 claims the priority benefit of ap. 62017615 filed on 2014 Jun. 26; ap. 15136948 claims the priority benefit of ap. 62089696 filed on 2014 Dec. 9; ap. 15236401 claims the priority benefit of ap. 62160172 filed on 2015 May 12; ap. 15236401 claims the priority benefit of ap. 62169661 filed on 2015 Jun. 2; ap. 15236401 claims the priority benefit of ap. 62303126 filed on 2016 Mar. 3; ap. 15236401 claims the priority benefit of ap. 62322594 filed on 2016 Apr. 14; ap. 15236401 is a CIP of ap. 14599522 filed on 2015 Jan. 18; ap. 14599522 claims the priority benefit of ap. 61932517 filed on 2014 Jan. 28; ap. 14599522 claims the priority benefit of ap. 61939244 filed on 2014 Feb. 12; ap. 14599522 claims the priority benefit of ap. 62017615 filed on 2014 Jun. 26; ap. 14599522 claims the priority benefit of ap. 62089696 filed on 2014 Dec. 9; ap. 15431769 is a CIP of ap. 15294746 filed on 2016 Oct. 16; ap. 15294746 is a CIP of ap. 14623337 filed on 2015 Feb. 16; ap. 14623337 claims the priority benefit of ap. 61944090 filed on 2014 Feb. 25; ap. 14623337 claims the priority benefit of ap. 61948124 filed on 2014 Mar. 5; ap. 14623337 claims the priority benefit of ap. 62100217 filed on 2015 Jan. 6; ap. 14623337 claims the priority benefit of ap. 62106856 filed on 2015 Jan. 23; ap. 14623337 claims the priority benefit of ap. 62111163 filed on 2015 Feb. 3; ap. 14623337 claims the priority benefit of ap. 62113423 filed on 2015 Feb. 7; ap. 14623337 claims the priority benefit of ap. 62115691 filed on 2015 Feb. 13; ap. 15294746 is a CIP of ap. 14951475 filed on 2015 Nov. 24; ap. 15294746 claims the priority benefit of ap. 62245311 filed on 2015 Oct. 23; ap. 15294746 claims the priority benefit of ap. 62349277 filed on 2016 Jun. 13; ap. 15431769 claims the priority benefit of ap. 62311462 filed on 2016 Mar. 22; ap. 15431769 claims the priority benefit of ap. 62349277 filed on 2016 Jun. 13; ap. 15431769 claims the priority benefit of ap. 62439147 filed on 2016 Dec. 26; ap. 15725330 is a CIP of ap. 14951475 filed on 2015 Nov. 24; ap. 14951475 is a CIP of ap. 13901131 filed on 2013 May 23; ap. 14951475 is a CIP of ap. 14071112 filed on 2013 Nov. 4; ap. 14951475 is a CIP of ap. 14623337 filed on 2015 Feb. 16; ap. 14951475 claims the priority benefit of ap. 62245311 filed on 2015 Oct. 23; ap. 15725330 claims the priority benefit of ap. 62549587 filed on 2017 Aug. 24; ap. 15725330 claims the priority benefit of ap. 62439147 filed on 2016 Dec. 26;

(C) is a CIP of ap. 14795373 filed on 2015 Jul. 9; ap. 14795373 is a CIP of ap. 14736652 filed on 2015 Jun. 11; ap. 14736652 is a CIP of ap. 14664832 filed on 2015 Mar. 21; ap. 14736652 claims the priority benefit of ap. 62100217 filed on 2015 Jan. 6; ap. 14736652 claims the priority benefit of ap. 62014747 filed on 2014 Jun. 20; ap. 14795373 claims the priority benefit of ap. 62187906 filed on 2015 Jul. 2; ap. 14795373 claims the priority benefit of ap. 62182473 filed on 2015 Jun. 20; ap. 14795373 claims the priority benefit of ap. 62086053 filed on 2014 Dec. 1; ap. 14795373 claims the priority benefit of ap. 62065032 filed on 2014 Oct. 17; and (D) claims the priority benefit of ap. 62683237 filed on 2018 Jun. 11.

The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to wearable sensors for human motion prediction and recognition.

INTRODUCTION

Electromyographic (EMG) sensors collect electromagnetic energy data concerning the activity of a person's muscles and the motor neurons which innervate these muscles. There are many potential applications for electromyographic sensor data. Wearable devices and/or clothing with electromyographic sensors which can collect electromyographic data relatively unobtrusively for extended periods of time can be particularly useful for a variety of innovative applications.

One application for electromyographic sensor data is sports and fitness. Sports and fitness applications can include: analyzing patterns of muscle exertion; estimating caloric expenditure and assisting in energy balance management; capturing, measuring, and recognizing full-body motion, posture, and configuration; comparing muscle activity with that of people in a peer group; detecting and correcting muscle group imbalances; enhancing athletic performance; guiding strength training; helping a person to perform a physical activity in a more efficient way; helping to avoid muscle fatigue and over-training; helping to prevent body injury; improving body posture and motion dynamics; improving fitness; monitoring nutritional intake; providing real-time feedback and/or coaching concerning physical activity; recognizing selected plays in athletic events for fan engagement and performance improvement; and recommending using different muscles.

Electromyographic sensor data can also be used for medical diagnostic and/or therapeutic purposes such as: analyzing gait and balance; assisting in energy balance management; avoiding injury from repeated motions; collecting and evaluating data concerning muscle activity and evaluating ergonomics; detecting and correcting muscle group imbalances; encouraging proper posture to avoid spinal injury; evaluating range of motion for selected muscles and/or associated body joints; evaluating skeletal muscle tension; guiding physical rehabilitation, occupational therapy, and/or physical therapy; helping a person to perform a physical activity in a safer manner; helping a person to perform a physical activity in a more therapeutic manner; helping to prevent falls and fractures; improving general fitness and health; measuring energy expenditure; monitoring nutritional intake; providing real-time feedback concerning a person's physical activity; recognizing changes in body configuration and posture; and tracking muscle fatigue.

Electromyographic sensor data can also be used for artistic and/or entertainment purposes such as: capturing, measuring, and recognizing full-body motion in order to animate an avatar or other virtual character in virtual reality, a computer game, an animated motion picture, or performance art; capturing dance moves for instruction or performance applications; and capturing the moves of a musician playing an instrument for instruction or performance applications.

Electromyographic sensor data can function as a Human-to-Computer Interface (HCI). It can be used for machine control and communication applications including: controlling a wearable device; controlling a mobile, laptop, or desktop computing device; controlling a prosthetic limb; controlling an appliance and/or security system; remote control of a robot (e.g. telerobotics); enabling teleconferencing and/or telepresence; predicting and recognizing human body motions; predicting and recognizing hand gestures; and translating sign language into words.

REVIEW OF THE RELEVANT ART

The most relevant art relates to the incorporation of electromyographic (EMG) sensors into wearable bands, belts or clothing. Relevant art which appears to disclose how EMG sensors can be incorporated into wearable bands or belts includes: U.S. Pat. No. 5,474,083 (Church et al., Dec. 12, 1995, "Lifting Monitoring and Exercise Training System"); U.S. Pat. No. 7,559,902 (Ting et al., Jul. 14, 2009, "Physiological Monitoring Garment"); U.S. Pat. No. 7,878,030 (Burr, Feb. 1, 2011, "Wearable Article with Band Portion Adapted to Include Textile-Based Electrodes and Method of Making Such Article"); U.S. Pat. No. 8,082,762 (Burr, Dec. 27, 2011, "Wearable Article with Band Portion Adapted to Include Textile-Based Electrodes and Method of Making Such Article"); U.S. Pat. No. 8,170,656 (Tan et al., May 1, 2012, "Wearable Electromyography-Based Controllers for Human-Computer Interface"); U.S. Pat. No. 9,037, 530 (Tan et al., May 19, 2015, "Wearable Electromyography-Based Human-Computer Interface"); and U.S. Pat. No. 9,039,613 (Kuck et al., May 26, 2015, "Belt with Sensors").

Band or belt type art also includes: U.S. Patent Applications 20050054941 (Ting et al., Mar. 10, 2015, "Physiological Monitoring Garment"); 20090229039 (Kuck et al., Sep. 17, 2009, "Belt with Sensors"); 20090326406 (Tan et al., Dec. 31, 2009, "Wearable Electromyography-Based Controllers for Human-Computer Interface"); 20100041974 (Ting et al., Feb. 18, 2010, "Physiological Monitoring Garment"); 20120188158 (Tan et al., Jul. 26, 2012, "Wearable Electromyography-Based Human-Computer Interface"); 20140198034 (Bailey et al., Jul. 17, 2014, "Muscle Interface Device and Method for Interacting with Content Displayed on Wearable Head Mounted Displays"); 20140198035 (Bailey et al., Jul. 17, 2014, "Wearable Muscle Interface Systems, Devices and Methods That Interact with Content Displayed on an Electronic Display"); 20140240103 (Lake et al., Aug. 28, 2014, "Methods and Devices for Combining Muscle Activity Sensor Signals and Inertial Sensor Signals for Gesture-Based Control"); 20140240223 (Lake et al., Aug. 28, 2014, "Method and Apparatus for Analyzing Capacitive EMG and IMU Sensor Signals for Gesture Control"); 20140334083 (Bailey, Nov. 13, 2014, "Systems, Articles and Methods for Wearable Electronic Devices That Accommodate Different User Forms"); 20150025355 (Bailey et al., Jan. 22, 2015, "Systems, Articles and Methods for Strain Mitigation in Wearable Electronic Devices"); and 20150051470 (Bailey et al., Feb. 19, 2015, "Systems, Articles and Methods for Signal Routing in Wearable Electronic Devices").

Band or belt type art also includes: U.S. Patent Applications 20150057506 (Luna et al., Feb. 26, 2015, "Arrayed Electrodes in a Wearable Device for Determining Physiological Characteristics"); 20150057770 (Bailey et al., Feb. 26, 2015, "Systems, Articles, and Methods for Human-Electronics Interfaces"); 20150065840 (Bailey, Mar. 5, 2015, "Systems, Articles, and Methods for Stretchable Printed Circuit Boards"); 20150070270 (Bailey et al., Mar. 12, 2015, "Systems, Articles, and Methods for Electromyography-Based Human-Electronics Interfaces"); 20150084860 (Aleem et al., Mar. 26, 2015, "Systems, Articles, and Methods for Gesture Identification in Wearable Electromyography Devices"); 20150109202 (Ataee et al., Apr. 23, 2015, "Systems, Articles, and Methods for Gesture Identification in Wearable Electromyography Devices"); 20150124566 (Lake et al., May 7, 2015, "Systems, Articles and Methods for Wearable Electronic Devices Employing Contact Sensors"); 20150141784 (Morun et al., May 21, 2015, "Systems, Articles, and Methods for Capacitive Electromyography Sensors"); 20150148641 (Morun et al., May 28, 2015, "Systems, Articles, and Methods for Electromyography Sensors"); and 20150169074 (Ataee et al., Jun. 18, 2015, "Systems, Articles, and Methods for Gesture Identification in Wearable Electromyography Devices").

Art which appears to disclose how EMG sensors can be incorporated into articles of clothing includes: U.S. Pat. No. 7,152,470 (Impio et al., Dec. 26, 2006, "Method and Outfit for Measuring of Action of Muscles of Body"); U.S. Pat. No. 7,559,902 (Ting et al., Jul. 14, 2009, "Physiological Monitoring Garment"); U.S. Pat. No. 7,878,030 (Burr, Feb. 1, 2011, "Wearable Article with Band Portion Adapted to Include Textile-Based Electrodes and Method of Making Such Article"); U.S. Pat. No. 8,082,762 (Burr, Dec. 27, 2011, "Wearable Article with Band Portion Adapted to Include Textile-Based Electrodes and Method of Making Such Article"); U.S. Pat. No. 8,162,857 (Lanfermann et al., Apr. 24, 2012, "Limb Movement Monitoring System"); U.S. Pat. No. 8,170,656 (Tan et al., May 1, 2012, "Wearable Electromyography-Based Controllers for Human-Computer Interface"); U.S. Pat. No. 8,185,231 (Fernandez, May 22, 2012, "Reconfigurable Garment Definition and Production Method"); 8945328 (Longinotti-Buitoni et al., Feb. 3, 2015, "Methods of Making Garments Having Stretchable and Conductive Ink"); 8948839 (Longinotti-Buitoni et al., Feb. 3, 2015, "Compression Garments Having Stretchable and Conductive Ink"); and U.S. Pat. No. 9,037,530 (Tan et al., May 19, 2015, "Wearable Electromyography-Based Human-Computer Interface").

Clothing type art also includes: U.S. Patent Applications 20050054941 (Ting et al., Mar. 10, 2015, "Physiological Monitoring Garment"); 20090326406 (Tan et al., Dec. 31, 2009, "Wearable Electromyography-Based Controllers for Human-Computer Interface"); 20100036288 (Lanfermann et al., Feb. 11, 2010, "Limb Movement Monitoring System"); 20100041974 (Ting et al., Feb. 18, 2010, "Physiological Monitoring Garment"); 20110166491 (Sankai, Jul. 7, 2011, "Biological Signal Measuring Wearing Device and Wearable Motion Assisting Apparatus"); 20120188158 (Tan et al., Jul. 26, 2012, "Wearable Electromyography-Based Human-Computer Interface"); 20130211208 (Varadan et al., Aug. 15, 2013, "Smart Materials, Dry Textile Sensors, and Electronics Integration in Clothing, Bed Sheets, and Pillow Cases for Neurological, Cardiac and/or Pulmonary Monitoring"); and 20130317648 (Assad., Nov. 28, 2013, "Biosleeve Human-Machine Interface").

Clothing type art also includes: U.S. Patent Applications 20140070957 (Longinotti-Buitoni et al., Mar. 13, 2014, "Wearable Communication Platform"); 20140135593 (Jayalth et al., May 15, 2014, "Wearable Architecture and Methods for Performance Monitoring, Analysis, and Feedback"); 20140142459 (Jayalth et al., May 22, 2014, "Wearable Performance Monitoring, Analysis, and Feedback Systems and Methods"); 20140213929 (Dunbar, Jul. 31, 2014, "Instrumented Sleeve"); 20140318699 (Longinotti-Buitoni et al., Oct. 30, 2014, "Methods of Making Garments Having Stretchable and Conductive Ink"); 20140378812 (Saroka et al., Dec. 25, 2014, "Thoracic Garment of Positioning Electromagnetic (EM) Transducers and Methods of Using Such Thoracic Garment"); 20150040282 (Longinotti-Buitoni et al., Feb. 12, 2015, "Compression Garments Having Stretchable and Conductive Ink"); 20150045699 (Mokaya et al., Feb. 12, 2015, "Musculoskeletal Activity Recognition System and Method"); 20150143601 (Longinotti-Buitoni et al., May 28, 2015, "Garments Having Stretchable and Conductive Ink"); and 20150148619 (Berg et al., May 28, 2015, "System and Method for Monitoring Biometric Signals").

SUMMARY OF THE INVENTION

This invention is a wearable circumferential array of electromyographic (EMG) sensors with a plurality of rings and columns of electromyographic sensors which collect electromagnetic energy data concerning neuromuscular activity. It can function as a Human-to-Computer Interface (HCI). In an example, it can be worn around a person's arm and/or wrist. In an example, it can be worn around a person's leg and/or ankle. In an example, it can be worn on a person's finger.

In an example, a circumferential array of electromyographic sensors can be incorporated into a wearable device or clothing accessory such as an arm band, wrist band, leg band, ankle band, bracelet, finger ring, or watch strap. In an example, a circumferential array of electromyographic sensors can be incorporated into the cuff or sleeve of an article of clothing such as a shirt or a pair of shorts. Different sensing roles can be assigned to different electromyographic sensors around the circumference of a body member in order to virtually correct for physical shifting or rotation of these electromyographic sensors around the body member.

INTRODUCTION TO THE FIGURES

DETAILED DESCRIPTION OF THE FIGURES

Figure 1:
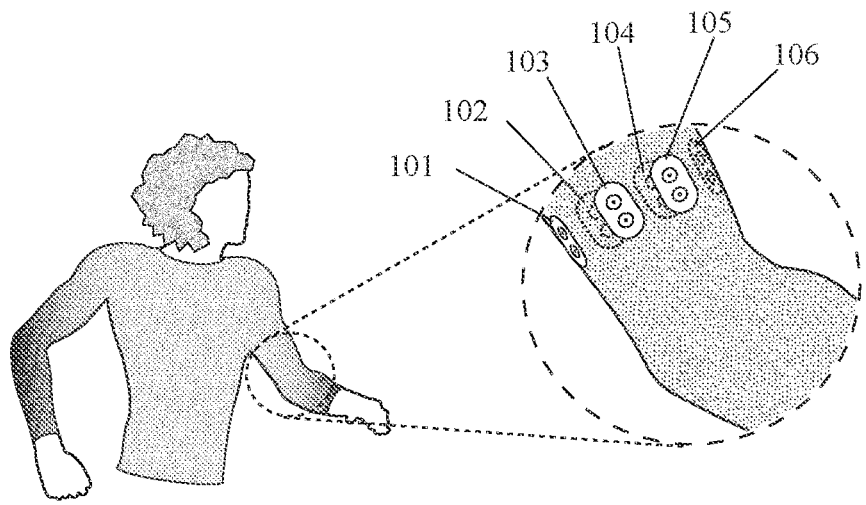
FIG. 1 shows a circumferential array of electromyographic sensors around a person's arm.

A circumferential array of electromyographic (EMG) sensors can be configured to be worn around a person's arm (and/or wrist), finger, or leg (and/or ankle) to collect electromagnetic energy data concerning activity of the person's nerves and muscles. In an example, a circumferential array of electromyographic sensors can function as a Human-to-Computer Interface (HCI). In an example, a circumferential array of electromyographic sensors can function as means of ambulatory human motion prediction and capture.

In an example, a circumferential array of electromyographic sensors can be incorporated into a wearable device and/or clothing accessory. In an example, a circumferential array of electromyographic sensors can be incorporated into an arm band or wrist band. In an example, a circumferential array of electromyographic sensors can be incorporated into a bracelet or bangle. In an example, a circumferential array of electromyographic sensors can be incorporated into a watch strap. In an example, a circumferential array of electromyographic sensors can be incorporated into a finger ring. In an example, a circumferential array of electromyographic sensors can be attached to a body member (such as an arm, wrist, finger, leg, or ankle) by connecting two ends of a wearable device and/or clothing accessory around the body member with a clasp, clip, buckle, hook, pin, plug, or hook-and-eye mechanism. In an example, a device comprising circumferential array of electromyographic sensors can be attached to a body member by stretching and sliding the device over the distal end of the body member.

In an example, a circumferential array of electromyographic sensors can be incorporated into an article of clothing. In an example, electromyographic sensors can be incorporated into the cuff of a (short sleeve) shirt. In an example, a circumferential array of electromyographic sensors can be incorporated into an elastic and/or stretchable cuff of a shirt. In an example, electromyographic sensors can be incorporated into the upper portion of a shirt sleeve. In an example, a circumferential array of electromyographic sensors can be incorporated into the cuff of a pair of shorts (or pants). In an example, a circumferential array of electromyographic sensors can be incorporated into an elastic and/or stretchable cuff of a pair of shorts or pants.

In an example, a circumferential array of electromyographic sensors can comprise a single ring of sensors, wherein this ring of sensors spans the entire circumference of a body member and wherein the body member is selected from the group consisting of an arm, wrist, hand, finger, leg, ankle, and foot. In an example, a circumferential array of electromyographic sensors can comprise a ring of sensors which spans between 50% and 75% of the circumference of a body member. In an example, a circumferential array of electromyographic sensors can comprise a ring of sensors which spans between 75% and 90% of the circumference of a body member.

In an example, a circumferential array of electromyographic sensors can comprise a plurality of rings of sensors, each of which spans the circumference of the body member. In an example, a circumferential array of electromyographic sensors can comprise two rings of sensors, each of which spans the circumference of a person's arm, wrist, hand, finger, leg, ankle, or foot. In an example, rings of sensors can be parallel to each other. In an example, a circumferential array of electromyographic sensors can comprise three rings of sensors, each of which spans the circumference of a person's arm, wrist, hand, finger, leg, ankle, or foot. In an example, a circumferential array of electromyographic sensors can comprise four or more rings of sensors.

In this disclosure, proximal means closer to a person's heart and distal means farther from the person's heart, when the person's body is in Vitruvian Man configuration (per Leonardo da Vinci). In an example, a circumferential array of electromyographic sensors can comprise sensors on different rings which are substantially parallel to a common longitudinal (proximal to distal) axis of a body member and thus form longitudinal (proximal to distal) columns of sensors. In an example, a circumferential array of electromyographic sensors can have rings and columns of sensors. In an example, a given sensor can be part of a ring of sensors in a circumferential direction and part of a column of sensors in a longitudinal direction.

In an example, a circumferential array of electromyographic sensors can have at least three rings and at least three columns of sensors. In an example, rings of sensors can span a body member in a generally circumferential (or partially circumferential) manner and columns of sensors can span the body member in a generally longitudinal (proximal-to-distal) manner. In an example, rings and columns of electromyographic sensors can form a three-dimensional array, grid, and/or matrix of sensors. In an example, a three-dimensional array, grid, and/or matrix of electromyographic sensors can have a shape selected from the group consisting of: cylindrical; frustal; hemi-cylindrical; hemi-frustal; melted ellipse and/or saddle shape.

A circumferential array of electromyographic sensors can comprise: at least three circumferential rings of electromyographic sensors which are configured to encircle a selected body member wherein the selected body member is selected from the group consisting of the person's arm, wrist, hand, finger, leg, ankle, or foot, and wherein electromyographic sensors in a ring of electromyographic sensors are at different polar coordinate locations around a circumference of the selected body member; and at least three of columns of electromyographic sensors which are configured to be substantially parallel to a longitudinal axis of the selected body member. In an example, different rings of sensors can be located at different places along a longitudinal (e.g. proximal to distal) axis of a body member. In an example, different rings of sensors can be located at different distances from a joint on the body member. In an example, a circumferential array of electromyographic sensors can be arranged in a plurality of circumferential rings, wherein each ring is configured to be a different distance along the longitudinal axis of a person's arm, wrist, hand, finger, leg, ankle, or foot.

In an example, a wearable device holding a circumferential array of electromyographic sensors can have radial undulations (or waves), wherein some portions or segments of the device are closer to the surface of a body member and some portions of the device are farther from the surface of the body member. In an example, a wearable device holding a circumferential array of electromyographic sensors can have radial undulations (or waves), wherein some portions or segments of the device are closer to the centroid of the device and some portions or segments of the device are farther from the centroid. In an example, the number of undulations (or waves) can equal the number of sensors. In an example, the number of undulations (or waves) can equal the number of sensors plus one. In an example, electromyographic sensors can be placed on inward-curving portions of radial undulations (or waves).

In an example, a wearable device holding a circumferential array of electromyographic sensors can have radial sinusoidal undulations. In an example, sensors can be placed on inward-curving portions of sinusoidal undulations. In an example, a wearable device can comprise a circumferential series of convex and concave segments. In an example, electromyographic sensors can be located on concave segments. Alternatively, electromyographic sensors can be located on the convex segments. In an example, electromyographic sensors can be located at the mid-points of concave segments. Alternatively, electromyographic sensors can be located at the mid-points of convex segments.

In an example, a wearable device holding a circumferential array of electromyographic sensors can have lateral undulations (or waves). In an example, the lateral width of a wearable device can vary at different points around the circumference of the device. In an example, the distal perimeter of a device can have undulations. In an example, these undulations can be sinusoidal undulations. In an example, the proximal perimeter of a device can have undulations. In an example, these undulations can be sinusoidal undulations. In an example, the distal and proximal perimeters of a wearable device can comprise sinusoidal waves which are 180-degrees out of phase with each other. In an example, the distal and proximal perimeters of a wearable device can comprise sinusoidal waves which are in phase with each other.

In an example, electromyographic sensors can be located on wider portions of a laterally-undulating wearable device. In an example, a circumferential array of electromyographic sensors can be located on the insides of wider portions in a laterally-undulating wearable device. In an example, the number of lateral undulations in a wearable device can equal the number of electromagnetic sensors in the device. In an example, the number of lateral undulations in a wearable device can equal the number of electromagnetic sensors in the device plus one. In an example, a wearable device can have circumferential variation in width, comprising a series of wider and narrower portions or segments around the circumference of the device. In an example, electromyographic sensors can be located on the inside surfaces of wider portions or segments.

In an example, the distance between adjacent rings of sensors in a circumferential array of sensors can be equal. In an example, the distance between the most proximal pair of adjacent rings of sensors in an circumferential array can be greater than the distance between the most distal pair of adjacent rings of sensors in the array. In an example, the distance between the most distal pair of adjacent rings of sensors in an circumferential array can be greater than the distance between the most proximal pair of adjacent rings of sensors in the array. In an example, the distance between the most proximal pair of adjacent rings of sensors in an circumferential array can be at least 25% greater than the distance between the most distal pair of adjacent rings of sensors in the array. In an example, the distance between the most distal pair of adjacent rings of sensors in an circumferential array can be at least 25% greater than the distance between the most proximal pair of adjacent rings of sensors in the array. In an example, distances between adjacent rings of sensors in a circumferential array of sensors can be adjusted. In an example, distances between adjacent rings of sensors in a circumferential array of sensors can be adjusted by a means selected from the group consisting of: electromagnetic actuator; inflatable chamber or pneumatic member; hydraulic mechanism; and adjustable spring.

In an example, the size of rings of sensors in a circumferential array of sensors can be equal. In an example, the size of the most proximal ring of sensors in an circumferential array can be greater than the size of the most distal ring of sensors in the array. In an example, the size of the most distal ring of sensors in an circumferential array can be greater than the size of the most proximal ring of sensors in the array. In an example, the size of the most proximal ring of sensors in an circumferential array can be at least 25% greater than the size of the most distal ring of sensors in the array. In an example, the size of the most distal ring of sensors in an circumferential array can be at least 25% greater than the size of the most proximal ring of sensors in the array. In an example, the sizes of rings of sensors in a circumferential array of sensors can be adjusted. In an example, the sizes of rings of sensors in a circumferential array of sensors can be adjusted by a means selected from the group consisting of: electromagnetic actuator; inflatable chamber or pneumatic member; hydraulic mechanism; and adjustable spring.

In an example, the elasticity level of bands or straps holding rings of sensors in a circumferential array of sensors can be equal. In an example, the elasticity level of a band or strap holding the most proximal ring of sensors in an circumferential array can be greater than the elasticity level of a band or strap holding the most distal ring of sensors in the array. In an example, the elasticity level of a band or strap holding the most distal ring of sensors in an circumferential array can be greater than the elasticity level of a band or strap holding the most proximal ring of sensors in the array. In an example, the elasticity level of a band or strap holding the most proximal ring of sensors in an circumferential array can be at least 25% greater than the elasticity level of a band or strap holding the most distal ring of sensors in the array. In an example, the elasticity level of a band or strap holding the most distal ring of sensors in an circumferential array can be at least 25% greater than the elasticity level of a band or strap holding the most proximal ring of sensors in the array. In an example, the elasticity levels of bands or straps holding rings of sensors in a circumferential array of sensors can be adjusted. In an example, the elasticity levels of bands or straps holding rings of sensors in a circumferential array of sensors can be adjusted by a means selected from the group consisting of: electromagnetic actuator; inflatable chamber or pneumatic member; hydraulic mechanism; and adjustable spring.

In an example, the tension of bands or straps holding rings of sensors in a circumferential array of sensors can be equal. In an example, the tension of a band or strap holding the most proximal ring of sensors in an circumferential array can be greater than the tension of a band or strap holding the most distal ring of sensors in the array. In an example, the tension of a band or strap holding the most distal ring of sensors in an circumferential array can be greater than the tension of a band or strap holding the most proximal ring of sensors in the array. In an example, the tension of a band or strap holding the most proximal ring of sensors in an circumferential array can be at least 25% greater than the tension of a band or strap holding the most distal ring of sensors in the array. In an example, the tension of a band or strap holding the most distal ring of sensors in an circumferential array can be at least 25% greater than the tension of a band or strap holding the most proximal ring of sensors in the array. In an example, the tensions of bands or straps holding rings of sensors in a circumferential array of sensors can be adjusted. In an example, the tensions of bands or straps holding rings of sensors in a circumferential array of sensors can be adjusted by a means selected from the group consisting of: electromagnetic actuator; inflatable chamber or pneumatic member; hydraulic mechanism; and adjustable spring.

In an example, the distance between sensors in a ring of sensors in a circumferential array of sensors can be equal. In an example, the distance between sensors in the most proximal ring of sensors in an circumferential array can be greater than the distance between sensors in the most distal ring of sensors in the array. In an example, the distance between sensors in the most distal ring of sensors in an circumferential array can be greater than the distance between sensors in the most proximal ring of sensors in the array. In an example, the distance between sensors in the most proximal ring of sensors in an circumferential array can be at least 25% greater than the distance between sensors in the most distal ring of sensors in the array. In an example, the distance between sensors in the most distal ring of sensors in an circumferential array can be at least 25% greater than the distance between sensors in the most proximal ring of sensors in the array. In an example, distances between sensors in a circumferential array can be adjusted. In an example, distances between sensors in a circumferential array of sensors can be adjusted by a means selected from the group consisting of: electromagnetic actuator; inflatable chamber or pneumatic member; hydraulic mechanism; and adjustable spring.

In an example, the distance between sensors on the portion of a ring of sensors spanning the dorsal surface of a body member can be greater than the distance between sensors on the portion of a ring of sensors spanning the ventral surface of the body member. In an example, the distance between sensors on the portion of a ring of sensors spanning the ventral surface of a body member can be greater than the distance between sensors on the portion of a ring of sensors spanning the dorsal surface of the body member. In an example, the distance between sensors on the portion of a ring of sensors spanning the dorsal surface of a body member can be at least 25% greater than the distance between sensors on the portion of a ring of sensors spanning the ventral surface of the body member. In an example, the distance between sensors on the portion of a ring of sensors spanning the ventral surface of a body member can be at least 25% greater than the distance between sensors on the portion of a ring of sensors spanning the dorsal surface of the body member.

In an example, the distance between sensors on the portion of a ring of sensors spanning the ventral or dorsal surfaces of a body member can be greater than the distance between sensors on the portion of a ring of sensors spanning the lateral surfaces of the body member. In an example, the distance between sensors on the portion of a ring of sensors spanning the lateral surfaces of a body member can be greater than the distance between sensors on the portion of a ring of sensors spanning the ventral or dorsal surfaces of the body member.

In an example, electromyographic sensors in a circumferential array can be compelled radially inward by an elastic band, wherein these sensors are pushed or pulled into close proximity to (and/or electromagnetic communication with) the surface of a body member. In an example, electromyographic sensors in a circumferential array can be pushed or pulled radially inward by a spring mechanism, wherein these sensors are pushed or pulled into close proximity to (and/or electromagnetic communication with) the surface of a body member. In an example, the wearer can change the proximity and/or force of the electromyographic sensors relative to the surface of a body member by adjusting a spring mechanism.

In an example, electromyographic sensors in a circumferential array can be compelled radially inward by a hydraulic mechanism, wherein these sensors are pushed into close proximity to (and/or electromagnetic communication with) the surface of a body member. In an example, the wearer can change the proximity and/or force of the electromyographic sensors relative to the surface of a body member by adjusting a hydraulic mechanism. In an example, electromyographic sensors in a circumferential array can be compelled radially inward by a pneumatic mechanism (e.g. balloon or air chamber), wherein these sensors are pushed into close proximity to (and/or electromagnetic communication with) the surface of a body member. In an example, the wearer can change the proximity and/or force of the electromyographic sensors relative to the surface of a body member by adjusting a pneumatic mechanism (e g inflating or deflating a balloon or air chamber). In an example, electromyographic sensors in a circumferential array can be compelled radially inward by an electromagnetic actuator (e.g. micro motor), wherein these sensors are pushed into close proximity to (and/or electromagnetic communication with) the surface of a body member. In an example, the wearer can change the proximity and/or force of the electromyographic sensors relative to the surface of a body member by activating an electromagnetic actuator (e.g. micro motor).

In an example, the size of sensors in a circumferential array of sensors can be uniform. In an example, the size of proximal sensors in a circumferential array can be greater than the size of distal sensors in the array. In an example, the size of distal sensors in a circumferential array can be greater than the size of proximal sensors in the array. In an example, the size of proximal sensors in a circumferential array can be at least 25% greater than the size of distal sensors in the array. In an example, the size of distal sensors in a circumferential array can be at least 25% greater than the size of proximal sensors in the array.

In an example, the size of ventral sensors in a circumferential array can be greater than the size of dorsal sensors in the array. In an example, the size of dorsal sensors in a circumferential array can be greater than the size of ventral sensors in the array. In an example, the size of ventral or dorsal surface sensors in a circumferential array can be greater than the size of lateral surface sensors in the array. In an example, the size of lateral surface sensors in a circumferential array can be greater than the size of ventral or dorsal surface sensors in the array.

In an example, a circumferential array of electromyographic sensors can function as a removable watch strap. In an example, a circumferential array of electromyographic sensors can function as a watch strap with removable connections to primary electronics housing with a display. In an example, a circumferential array of electromyographic sensors can comprise a single ring of sensors which spans between 75% and 90% of the circumference of a body member selected from the group consisting of a person's arm, wrist, hand, finger, leg, ankle, and foot. In an example, a circumferential array of electromyographic sensors can comprise a plurality of rings of sensors, each of which spans between 75% and 90% of the circumference of a body member.

In an example, a circumferential array of electromyographic sensors can function as a bracelet. In an example, a circumferential array of electromyographic sensors can comprise a single ring of sensors which spans between 50% and 75% of the circumference of a body member selected from the group consisting of a person's arm, wrist, hand, finger, leg, ankle, and foot. In an example, a circumferential array of electromyographic sensors can comprise a plurality of rings of sensors, each of which spans between 50% and 75% of the circumference of a body member.

In an example, a circumferential array of electromyographic sensors can encircle a body member (e.g. arm, wrist, hand, finger, leg, ankle, or foot) at different polar coordinate locations around the circumference of the body member. In an example, these polar-coordinate locations can be evenly spaced around the circumference of the body member. In an example, these polar-coordinate locations can be unevenly spaced around the circumference of the body member. In an example, electromyographic sensors in a circumferential array of electromyographic sensors can be disproportionately located (e.g. clustered) on the ventral and dorsal surfaces of the body member. In an example, electromyographic sensors in a circumferential array of electromyographic sensors can be disproportionately located (e.g. clustered) on the ventral and lateral surfaces of the body member. In an example, electromyographic sensors in a circumferential array of electromyographic sensors can be disproportionately located (e.g. clustered) on the dorsal and lateral surfaces of the body member.

In an example, a circumferential array of electromyographic sensors can comprise a single ring of six electromagnetic sensors distributed around the circumference of a body member. In an example, a circumferential array of electromyographic sensors can comprise a plurality of rings, wherein each ring further comprises six electromagnetic sensors distributed around the circumference of a body member. In an example, a circumferential array of electromyographic sensors can comprise a ring of eight electromagnetic sensors distributed around the circumference of a body member. In an example, a circumferential array of electromyographic sensors can comprise a plurality of rings, wherein each ring further comprises eight electromagnetic sensors distributed around the circumference of a body member. In an example, different rings in a circumferential array of electromyographic sensors can have different numbers of sensors. In an example, proximal rings can have more sensors than distal rings. In an example, proximal rings can have fewer sensors than distal rings.

In an example, different sensing roles can be assigned to different electromyographic sensors around the circumference of the selected body member in order to virtually correct for physical shifting or rotation of these electromyographic sensors around the selected body member. In an example, data from a circumferential array of electromyographic sensors can be analyzed to identify which sensor is closest to which nerve or muscle. In an example, data from a circumferential array of electromyographic sensors can be analyzed to virtually correct for circumferential rotation or other circumferential positional variation of the array around the body member. In an example, data from a circumferential array of electromyographic sensors can be analyzed to virtually correct for longitudinal (e.g. proximal to distal) sliding or other longitudinal positional variation of the array along the body member.

In an example, data from a circumferential array of electromyographic sensors can be analyzed using a Hidden Markov Model (HMM) or other Markov modeling. In an example, data from a circumferential array of electromyographic sensors can be analyzed using Bayesian analysis. In an example, data from a circumferential array of electromyographic sensors can be analyzed using a neural network. In an example, data from a circumferential array of electromyographic sensors can be analyzed using a back propagation network. In an example, data from a circumferential array of electromyographic sensors can be analyzed using least squares estimation.

In an example, a plurality of electromyographic sensors can be held in place by a plurality of electronics housings. In an example, a circumferential array of electromyographic sensors can be held in place by a circumferential array of inter-connected electronics housings. In an example, a circumferential array of electromyographic sensors can comprise: a circumferential array of electronics housings which are configured to encircle a selected body member of a person (wherein the selected body member is selected from the group consisting of the person's arm, wrist, hand, finger, leg, ankle, or foot) and wherein electronics housings in a ring of electromyographic housings are at different polar coordinate locations around a circumference of the selected body member; and a circumferential array of electromyographic sensors which are configured to be held on the selected body member by the circumferential array of electronics housings. In an example, there can also be a circumferential array of pairs of flexible members which interconnect the electronics housings. In an example, there can be a gap between flexible members in a pair of flexible members to let air through. In an example, flexible members can be selected from the group consisting of bands, straps, strips, swatches, wires, cords, threads, joints, and chain links.

In an example, an electromyographic sensor in a circumferential array of electromyographic sensors can comprise a low-conductivity material which has been doped, impregnated, or coated with a high-conductivity material. In an example, an electromyographic sensor in a circumferential array of electromyographic sensors can comprise a dielectric layer of low-conductivity material between two layers of high-conductivity material. In an example, an electromyographic sensor in a circumferential array of electromyographic sensors can comprise a layer of high-conductivity material between two layers of low-conductivity material. In an example, an electromyographic sensor in a circumferential array of electromyographic sensors can comprise a low-conductivity lumen filled with a high-conductivity fluid. In an example, an electromyographic sensor in a circumferential array of electromyographic sensors can comprise low-conductivity fibers and highly-conductive fibers which are braided or woven together.

In an example, an electromyographic sensor can be made with a low-conductivity material selected from the group consisting of: acetate, acrylic, cotton, denim, elastane, latex, linen, Lycra™, neoprene, nylon, nylon, polyester, wool, silicone, polydimethylsiloxane (PDMS), silk, spandex, and rayon. In an example, an electromyographic sensor can be made with a high-conductivity material selected from the group consisting of: aluminum or aluminum alloy; carbon nanotubes, graphene, or other carbon-based material; copper or copper alloy; gold; nickel; silver; and steel. In an example, an electromyographic sensor can be made with polydimethylsiloxane (PDMS) which has been doped or impregnated with aluminum, carbon (in one or more various configurations and formulations), copper, gold, nickel, silver, or steel. In an example, an electromyographic sensor can be made from polydimethylsiloxane (PDMS) and carbon nanotubes. In an example, an electromyographic sensor can be made from polydimethylsiloxane (PDMS) and silver.

In an example, an electromyographic sensor can be made by printing a pattern with high-conductivity ink onto a low-conductivity textile or fabric. In an example, an electromyographic sensor can be made by (3D) printing an elastomeric conductive material onto a low-conductivity textile or fabric. In an example, an electromyographic sensor can be made by melting or adhering elastomeric conductive material onto a low-conductivity textile or fabric. In an example, an electromyographic sensor can be made by embroidering conductive material onto a low-conductivity textile or fabric. In an example, an electromyographic sensor can be made by inserting doped PDMS into the elastic band of a cuff on a shirt or pair of shorts.

FIG. 1 shows an example of a circumferential array of electromyographic sensors which are configured to collect electromagnetic energy data concerning the neuromuscular activity of a person's muscles. In this example, a circumferential array of electromyographic sensors is worn on a person's arm. In FIG. 1, electromyographic sensors 101, 102, 103, 104, 105, and 106 encircle a person's arm at different polar coordinate locations around the circumference of the person's arm. In an example, a circumferential array of electromyographic sensors can be incorporated into a clothing accessory or wearable device selected from the group consisting of: arm band, bangle, bracelet, finger ring, smart watch, watch strap, wrist band, and wrist watch. In an example, a circumferential array of electromyographic sensors can be incorporated into the cuff or sleeve of an article of clothing such as a shirt or pair of pants.

In an example, pattern recognition can be used to analyze data received from a circumferential array of electromyographic sensors in order to identify which sensors are at which polar coordinates around a person's arm. In this manner, a system can identify when a device has shifted (rotated) circumferentially around a person's arm and can virtually correct for such shifts (or rotations). In an example, a system can identify which electromyographic sensor is at which location based on signals from nearby specific muscles and/or nerves. In an example, a system can assign different sensing roles to different electromyographic sensors around the circumference of a person's arm in order to correct for physical shifting (or rotation) of a device around the person's arm.

In an example, a circumferential array of electromyographic sensors can be arranged in a series of circumferential rings and columns, wherein each ring is configured to be a different distance along a longitudinal axis of a body member and each column is configured to be parallel to a longitudinal axis of the body member. In an example, there can be at least three rings and at least three columns in a circumferential array of electromyographic sensors. This can enable accurate measurement of electromagnetic energy from specific nerves and muscles even if the device is rotated circumferentially around a person's arm or slid longitudinally (e.g. proximally to distally, or vice versa) along the person's arm. Relevant example variations discussed elsewhere in this disclosure or in priority-linked disclosures can also be applied to the example shown in this figure, but are not repeated here in order to reduce narrative redundancy.

Figure 2:
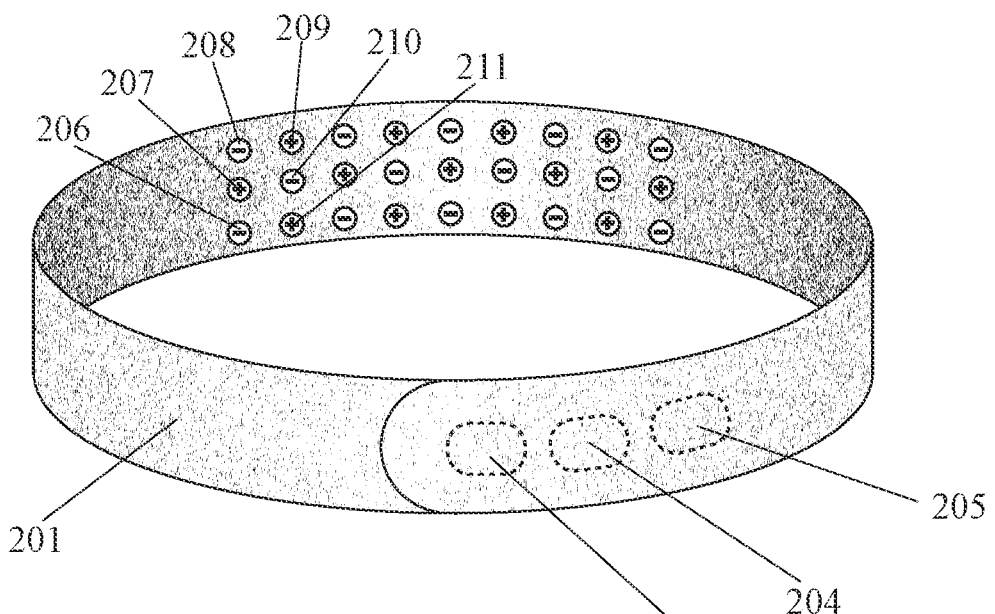
FIG. 2 shows a circumferential array of electromyographic sensors with a plurality of rings and columns of electromyographic sensors.

FIG. 2 shows another example of a circumferential array of sensors. FIG. 2 shows: an array with a first set of sensors (energy emitters and/or receivers in this example) along a first circumferential line of a wearable arcuate band, a second set of sensors along a second circumferential line of the wearable arcuate band, and a third set of sensors along a third circumferential line of the wearable arcuate band. In an example, electromyographic sensors in different rings along a common longitudinal (e.g. proximal to distal) line can form columns of electromyographic sensors. In an example, there can be a circumferential array, grid, or matrix of electromyographic sensors with at least three rows and at least three columns of electromyographic sensors.

FIG. 2 can also be described as showing: an arcuate band 201 which is configured to span the circumferential perimeter of a part of a person's body (such as a wrist, arm, finger, ankle, and/or leg); a first set of three or more energy emitters and/or receivers (including 208 and 209) along a first circumferential line of the arcuate band; a second set of three or more energy emitters and/or receivers (including 207 and 210) along a second circumferential line of the arcuate band; a third set of three or more energy emitters and/or receivers (including 206 and 211) along a third circumferential line of the arcuate band, wherein energy emitters are configured to emit energy toward the person's body and energy receivers are configured to receive energy from the person's body; a data processor 204 which receives data from the energy receivers; an energy source 203 which provides energy to the central energy emitter and/or to the data processor; and a data transmitter 205 which transmits data from the data processor to a remote device and/or remote location. Relevant example variations discussed elsewhere in this disclosure or in priority-linked disclosures can also be applied to the example shown in this figure, but are not repeated here in order to reduce narrative redundancy.

Figure 3:
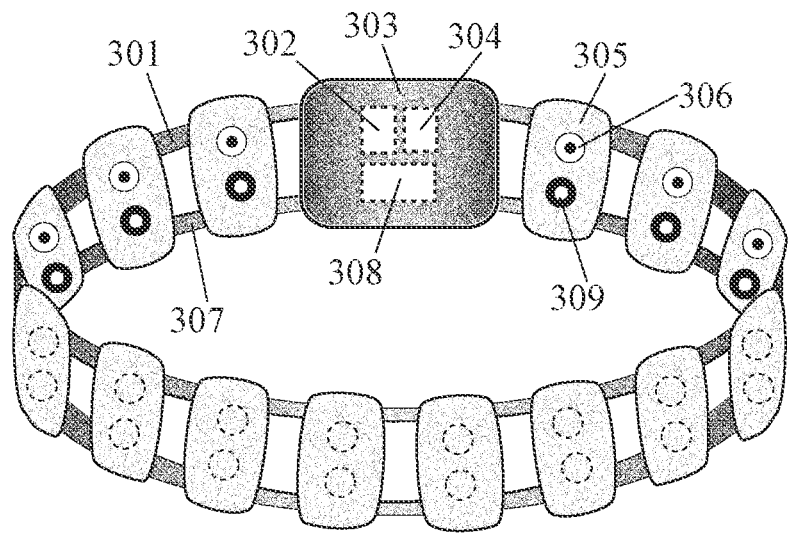
FIGS. 3 and 4 show two different views of a circumferential array of electromyographic sensors incorporated into a circumferential array of inter-connected electronics housings.
Figure 4:
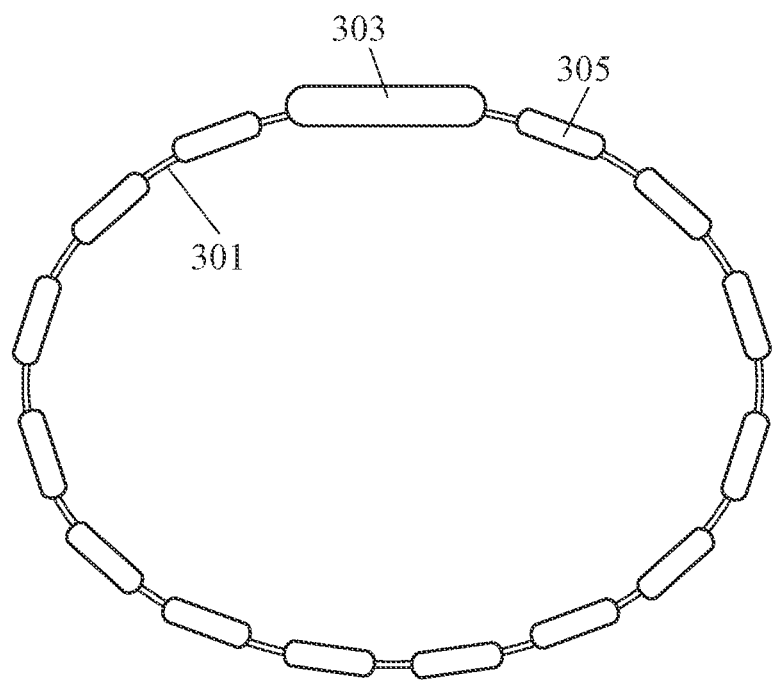

FIGS. 3 and 4 show another example of a circumferential array of sensors. In this example, electronics housings with biometric sensors are inter-connected by pairs of flexible bands with gaps between them. This allows for airflow to skin under the wearable band between electronics housings. FIG. 3 shows an opaque, oblique, side view. FIG. 4 shows a top-down, outline view of the same device. This device has a primary electronics housing on the dorsal surface on a person's wrist and/or arm (which may have an outward-facing watch display) and a circumferential series of secondary electronics housings (which have inward-facing biometric sensors). In an example, these biometric sensors can comprise a circumferential array of electromyographic sensors. The circumferential series of secondary electronics housings are connected to each other by pairs of two flexible members which are each separated from each other by a gap. These flexible members can be selected from the group consisting of bands, straps, strips, swatches, wires, cords, threads, joints, and chain links.

The circumferential array of sensors shown in FIGS. 3 and 4 can also be described as comprising: a primary electronics housing (303); a circumferential array of electronics housings (such as 305); energy emitting biometric sensors (such as 306); energy receiving sensors (such as 309) on the electronics housings; pairs of flexible members (such as 301 and 307) which connect pairs of housings; a data processor (302); a data transceiver (304); and a battery (308). In an example, the primary electronics housing can include a watch display on its outward-facing surface so that this wearable band functions as a smart watch. In an example, the series of flexible members and secondary electronics housings with biometric sensors can function as a watch band. Relevant example variations discussed elsewhere in this disclosure or in priority-linked disclosures can also be applied to the example shown in this figure, but are not repeated here in order to reduce narrative redundancy.

Figure 5:
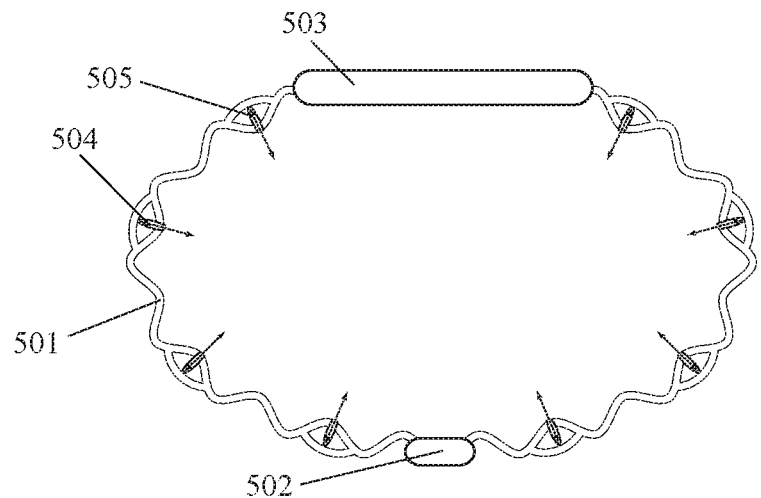
FIG. 5 shows an undulating watch strap with a circumferential array of electromyographic sensors.

FIG. 5 shows another example of a circumferential array of sensors. FIG. 5 shows the device from a side perspective, as it would appear encircling a lateral cross-section of a person's wrist (or other portion of the person's arm). Described generally, the example shown in FIG. 5 is a wearable device for the arm with a flexible circumferentially-undulating band with sensors on the proximal portions of undulating waves. A band with such a flexible circumferentially-undulating structure can help to keep a plurality of electromyographic sensors in close proximity to the surface of a person's arm. In an example, it can be a smart watch, watch band, arm band, wrist band, bracelet, ring, or armlet. In an example, it can have a repeating wave pattern. In an example, it can have a sinusoidal wave pattern.

The example shown in FIG. 5 is a circumferential array of sensors comprising: a circumferentially-undulating attachment member which is configured to span the circumference of a person's arm; and a plurality of sensors, wherein each sensor is located at the proximal portion of an undulation, and wherein the proximal portion of an undulation is the portion of an undulating wave which is closest to the circumferential center of the device.

With respect to specific components, the example shown in FIG. 5 includes: circumferentially-undulating band 501, band connector 502, electronics enclosure 503, first sensor 504 at the proximal portion of a first wave in the circumferentially-undulating band, and second sensor 505 at the proximal portion of a second wave in the circumferentially-undulating band. In an example, this device can further comprise one or more components selected from the group consisting of: a data processor; a battery and/or energy harvesting unit; a display screen; a data transmitter; and a data receiver. Relevant example variations discussed elsewhere in this disclosure or in priority-linked disclosures can also be applied to the example shown in this figure, but are not repeated here in order to reduce narrative redundancy.

Figure 6:
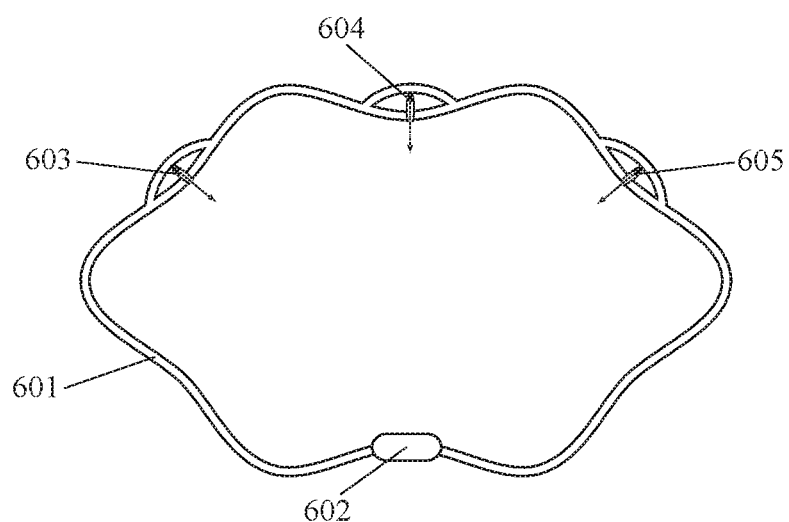
FIG. 6 shows an undulating band with a circumferential array of electromyographic sensors.

FIG. 6 shows another example of a circumferential array of sensors. This figure shows the device from a side perspective, as it would appear encircling a lateral cross-section of a person's wrist (or other portion of the person's arm). Described generally, the example shown in FIG. 6 is a wearable device for the arm with a flexible circumferentially-undulating band with six waves and sensors on the proximal portions of some or all of these waves.

A band with a circumferentially-undulating structure can help to keep a plurality of electromyographic sensors in close proximity to the surface of a person's arm. Further, a band with six waves can engage the sides of a person's wrist with two symmetrically-opposite waves to resist rotational shifting better than a circular or oval band. This can help to reduce measurement errors caused by movement of the sensors. In an example, it can be a smart watch, watch band, arm band, wrist band, bracelet, ring, or armlet. In an example, it can have a repeating wave pattern. In an example, it can have a sinusoidal wave pattern.

The example shown in FIG. 6 is a wearable device for the arm comprising: a circumferentially-undulating attachment member with six waves which is configured to span the circumference of a person's arm; and a plurality of sensors, wherein each sensor is located at the proximal portion of an undulation, and wherein the proximal portion of an undulation is the portion of an undulating wave which is closest to the circumferential center of the device.

With respect to specific components, the example shown in FIG. 6 includes: circumferentially-undulating band 601 with six waves, band connector 602, a first sensor 603 at the proximal portion of a first wave in the circumferentially-undulating band, a second sensor 605 at the proximal portion of a second wave in the circumferentially-undulating band, and a third sensor 606 at the proximal portion of a third wave in the circumferentially-undulating band. In an example, this device can further comprise one or more components selected from the group consisting of: a data processor; a battery and/or energy harvesting unit; a display screen; a data transmitter; and a data receiver. Relevant example variations discussed elsewhere in this disclosure or in priority-linked disclosures can also be applied to the example shown in this figure, but are not repeated here in order to reduce narrative redundancy.

Having discussed the examples shown in FIGS. 1 through 6, the following section provides additional elaboration on how a circumferential array of electromyographic sensors can be incorporated into an article of clothing or clothing accessory. Embodiment variations in the following section can be applied, where relevant, to the examples shown FIGS. 1 through 6. In an example, an array of electromyographic sensors can be incorporated into an article of electromyographic clothing selected from the group consisting of: bathrobe, bikini, blouse, boot, bra, briefs, cap, coat, dress, full-body article of clothing, garment with hood, girdle, glove, hat, hoodie, jacket, jeans, jockstrap, jumpsuit, leggings, leotards, long-sleeve shirt, lower-body garment, one-piece garment, overalls, pair of pants, pajamas, panties, pants, shirt, shorts, short-sleeve shirt, skirt, slacks, sock, suit, sweater, sweatpants, sweatshirt, sweat suit, swimsuit, tights, trousers, T-shirt, underpants, undershirt, union suit, upper-body garment, and vest.

In an example, an array of electromyographic sensors can be incorporated into a wearable device or clothing accessory selected from the group consisting of: abdominal brace, adhesive patch, amulet, ankle band, ankle brace, ankle bracelet, ankle strap, arm band, arm bracelet, artificial finger nail, bandage, bangle, beads, belt, bracelet, brooch, button, charm bracelet, chest band, chest strap, collar, contact lens, cuff link, dog tag, ear bud, ear muff, ear plug, ear ring, earphones, elastic band, elbow brace, elbow pad, electronic tattoo, eyeglasses, eyewear, face mask, finger nail attachment, finger ring, finger tube, fitness bracelet, fitness watch, footwear, forearm cuff, goggles, hair band, hair clip, hair pin, headband, headphones, hearing aid, helmet, knee brace, knee pad, leg band, monocle, neck band, neck chain, neck tie, necklace, nose ring, ornamental pin, pantyhose, patch, pendant, pin, pocketbook, poncho, sandal, shoe, shoulder brace, shoulder pad, skin patch, skullcap, sneaker, suspenders, tattoo, tie clip, visor, waist band, watch, wig, and wristband.

In an example, an article of electromyographic clothing can be configured to be worn on one or more portions of a person's body which are selected from the group consisting of: abdomen, ankle, arm, back, ear, elbow, eyes (directly such as via contact lens or indirectly such as via eyewear), finger, foot, forearm, hand, head, hip, jaw, knee, lips, lower arm, lower leg, mouth, neck, nose, palm, pelvis, rib cage, shoulder, spine, teeth, throat, thumb, toe, tongue, torso, upper arm, upper leg, waist, and wrist. In an example, an article of electromyographic clothing can be configured to collect data which is used to estimate the movement, angle, and/or configuration of one or more body joints. In an example, an electromyographic sensor can be configured to cover (the mid-section of) a muscle which is proximal or distal from a selected body joint.

In various examples, electromyographic clothing can be used to estimate, measure, predict, and/or model the abduction, extension, flexion, and/or ulnar deviation or radial deviation of a body joint. In various examples, electromyographic clothing can be used to measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

An article of electromyographic clothing can be configured to collect data concerning the electromagnetic energy which is emitted by muscles and/or by the nerves which innervate those muscles. In various examples, an article of electromyographic clothing can be configured to collect data concerning electromagnetic energy emitted by the neuromuscular activity of one or more of the following: abductor digiti minimi (brevis), abductor hallucis, abductor pollicis (longus), adductor (brevis, longus, magnus, minimus), adductor hallucis, adductor pollicis, anconeus, articularis genus, biceps brachii, biceps femoris, brachialis, brachioradialis, coracobrachialis, deltoid (anterior, lateral, posterior), deltoideus, extensor carpi radialis (brevis, longus), extensor carpi ulnaris, extensor digitorum (brevis, longus), extensor hallucis (brevis, longus), extensor indicis, extensor pollicis (brevis, longus), fibularis tertius, flexor carpi (radialis, ulnaris), flexor digitorum (brevis, minimi), flexor digitorum (profundus, superficialis), flexor hallucis (brevis, longus), flexor pollicis (brevis, longus), gastrocnemius (lateralis, medialis), gemellus (inferior, superior), gluteus bogus, gluteus maximus, gluteus medius, gluteus minimus, gracilis, iliacus, iliopsoas, infraspinatus, interossei (dorsal, palmer), lateralis of the sastrocnemius, levator scapulae, lumbrical, medialis of the gastrocnemius, obturator (externus, internus), opponens digiti minimi, opponens pollicis, palmaris (brevis, longus), pectineus, pectoralis (minor, major), peroneus brevis, peroneus longus, piriformis, plantaris, popliteus, pronator quadratus, pronator teres, psoas (major, minor), quadratus femoris, quadratus plantae, quadriceps femoris (rectus femoris, vastus lateralis, vastus medialis), rectus femoris of the quadriceps femoris, rhomboid (minor, major), sartorius, sastrocnemius, semimembranosus, semitendinosus, serratus (anterior), soleus, subclavius, subscapularis, supinator, supraspinatus, tensor fasciae latae, teres (minor, major), tibialis anterior, tibialis posterior, trapezius, triceps brachii, triceps surae, vastus intermedius, vastus lateralis of the quadriceps femoris, and vastus medialis of the quadriceps femoris.

In an example, one or more electromyographic sensors can be created as part of a fabric or textile which is then used to create an article of electromyographic clothing. In an example, one or more electromyographic sensors can be created as part of a fabric or textile by weaving, knitting, sewing, embroidering, layering, laminating, adhering, melting, fusing, printing, spraying, painting, cutting, or pressing electroconductive threads, yarns, fibers, strands, layers, inks, or resins. This fabric or textile can then be used to create an article of electromyographic clothing.

In an example, one or more electromyographic sensors can be created as part of an article of electromyographic clothing as the clothing is being made. In an example, one or more electromyographic sensors can be created by weaving, knitting, sewing, embroidering, layering, laminating, adhering, melting, fusing, printing, spraying, painting, or pressing electroconductive threads, yarns, fibers, strands, layers, inks, or resins as an article of electromyographic clothing is being made.

In an example, one or more electromyographic sensors can be permanently attached to (or formed on) an article of clothing after the clothing has been made. In an example, one or more electromyographic sensors can be attached to an article of clothing by insertion, hook-and-eye mechanism, sewing, embroidering, adhesion, melting, pressing, printing, snapping, clipping, pinning, or plugging. In an example, one or more modular electromyographic sensors can be removably-attached in different configurations to an article of electromyographic clothing by insertion, hook-and-eye mechanism, pressing, snapping, clipping, pinning, or plugging after the clothing has been made. In an example, one or more modular electromyographic sensors can be removably-attached in different configurations to an article of electromyographic clothing by insertion, hook-and-eye mechanism, pressing, snapping, clipping, pinning, or plugging by the person who wears the clothing.

In an example, the number, types, locations, orientation, and/or configurations of electromyographic sensors which are part of an article of electromyographic clothing can be customized and/or specifically configured to optimally collect data concerning the muscle activity of a specific person. In an example, the number, types, locations, orientation, and/or configurations of electromyographic sensors which are part of an article of electromyographic clothing can be customized and/or specifically configured to optimally collect data concerning muscle activity during a specific sport or other specific type of physical activity. In an example, customization of sensor configuration can occur while a fabric or textile is created, wherein this fabric or textile is then used to make an article of clothing. In an example, customization of sensor configuration can occur while an article of clothing is being made. In an example, customization of sensor configuration can occur after an article of clothing has been made.

In an example, customization of sensor configuration can be accomplished with modular components whose configuration is changed by a manufacturer, by a retailer, and/or by the person who wears the clothing. In an example, a manufacturer can combine and/or assemble a set of modular components into an article of electromyographic clothing in order to create an article which optimally measures muscle activity data from a specific person or during a specific type of physical activity. In an example, a clothing seller can combine and/or assemble a set of modular components into an article of electromyographic clothing in order to create an article which optimally measures muscle activity data from a specific person or during a specific type of physical activity. In an example, a clothing wearer can combine and/or assemble a set of modular components into an article of electromyographic clothing in order to create an article which optimally measures muscle activity data from a specific person or during a specific type of physical activity.

In an example, one or more electromyographic sensors can be created as part of an electronically-functional fabric or textile from which an article of electromyographic clothing is made. In an example, one or more electromyographic sensors can be created as part of an electronically-functional fabric or textile by weaving, knitting, sewing, embroidering, layering, laminating, adhering, melting, fusing, printing, spraying, painting, or pressing electroconductive material into (or onto) a fabric or textile. In an example, electromyographic sensors can be attached to (or created within) a fabric or textile by weaving, knitting, sewing, embroidering, layering, laminating, adhering, melting, fusing, printing, spraying, painting, or pressing. In an example, electroconductive threads, fibers, yarns, strands, filaments, traces, and/or layers within a fabric or textile can be configured near a person's skin in order to receive electromagnetic energy emitted by nerves and muscles below the skin.

In an example, one or more electromyographic sensors can be created as part of an article of clothing as that clothing is being made from conventional (non-electronic) fabric or textile. In an example, one or more electromyographic sensors can be created as part of an article of clothing by weaving, knitting, sewing, embroidering, layering, laminating, adhering, melting, fusing, printing, spraying, painting, or pressing electroconductive material into (or onto) the clothing while the clothing is being made. In an example, electromyographic sensors can be attached or created by weaving, knitting, sewing, embroidering, layering, laminating, adhering, melting, fusing, printing, spraying, painting, or pressing. In an example, electroconductive threads, fibers, yarns, strands, filaments, traces, and/or layers can be configured near a person's skin in order to receive electromagnetic energy emitted by nerves and muscles below the skin.

In an example, one or more electromyographic sensors can be attached to an article of clothing after a conventional article of clothing has been made. In an example, one or more electromyographic sensors can be attached to an article of clothing after the clothing has been made using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper. In an example, one or more electromyographic sensors can be created on an article of clothing after the article of clothing has been made by printing, laminating, adhering, embroidering, melting, and/or sewing electroconductive material onto the clothing after the basic form of the clothing has been made.

In an example, electromyographic clothing can be modular. In an example, modular electromyographic clothing can be constructed and/or adjusted so as to optimally collect data concerning the muscle activity of a specific person or muscle activity during a specific sport (or other type of physical activity). In an example, the number, type, location, orientation, and/or configuration of electromyographic sensors on (or within) an article of clothing can be selected, configured, customized, and/or adjusted so as to best collect data concerning the muscle activity of a specific person or muscle activity during a specific type of sport (or other physical activity). In an example, this selection, configuration, customization, and/or adjustment can occur during the creation of a fabric or textile from which the clothing is made, as the article of clothing is being made from a fabric or textile, or after the article of clothing has been made from a fabric or textile.

In an example, the selection, configuration, customization, and/or adjustment of electromyographic sensors can be done by a clothing or textile manufacturer, by a clothing retailer, or by a clothing user. In an example, electromyographic clothing can have modular components which are assembled by a manufacturer or retailer in order to create an article of electromyographic clothing which is customized and/or tailor made for a specific person or a specific type of physical activity. In an example, electromyographic clothing can have modular components which are selected, configured, customized, and/or adjusted by the person who wears the clothing in order to optimally measure the muscle activity of that specific person. In an example, electromyographic clothing can have modular components which are selected, configured, customized, and/or adjusted by a person participating in a specific sport (or other type of physical activity) in order to optimally measure the muscle activity during that specific sport (or other type of physical activity).

In an example a customized article of electromagnetic clothing can be created by attaching, clipping, connecting, plugging, inserting, and/or snapping modular electroconductive members onto an article of clothing. In an example, one or more electromyographic sensors can be attached (permanently or temporarily) to an article of electromyographic clothing by a mechanism selected from the group consisting of: a buckle, a button, a chain, a clamp, a clasp, a clip, a hook, a hook-and-eye mechanism, a magnet, a pin, a plug, a snap, a strap, a string, a tie, a zipper, an adhesive, an elastic band, an electronic plug, insertion into a channel, insertion into a pocket, insertion into a pouch, and tape.

In an example a customized article of electromagnetic clothing can be created by adhering, gluing, laminating, and/or melting modular electroconductive members onto an article of clothing. In an example a customized article of electromagnetic clothing can be created by weaving, knitting, sewing, embroidering, layering, laminating, adhering, melting, fusing, printing, spraying, painting, or pressing modular electroconductive members onto (or into) an article of clothing. In an example a customized article of electromagnetic clothing can be created by flocking, painting, printing, spraying, and/or screening modular electroconductive material onto an article of clothing. In an example a customized article of electromagnetic clothing can be created by inserting, pressing, rotating, and/or sliding modular electroconductive members onto (or across) the surface an article of clothing.

In an example, a customized modular article of electromyographic clothing can be created by: selecting a module from a first set of EMG sensor modules with the best sensor configuration for measuring muscle activity from a first body location for a specific person or sport; selecting a module from a second set of EMG sensor modules with the best sensor configuration for measuring muscle activity from a second body location for that specific person or sport; selecting a module from a third set of EMG sensor modules with the best sensor configuration for measuring muscle activity from a third body location for that specific person or sport; and combining these three selected modules into a single customized article of clothing. In an example, each module in each set can include at least one electromyographic sensor. Alternatively, there can be a set and/or module with no electromyographic sensors. A module with no electromyographic sensor can serve a variable-size placeholder in a longitudinal series of sets.

In an example, electroconductive threads, fibers, yarns, strands, filaments, traces, layers, inks, and/or resins can be made from one or more materials selected from the group consisting of: aluminum (Al), aluminum alloy, brass (Ms), carbon nanotubes, carbon-based material, ceramic particles, copper (Cu), copper alloy, copper-clad aluminum, fluorine, gold (Au), graphene, magnesium, nickel, niobium (Nb), organic solvent, polyaniline, polymer, rubber, silicone, silver (Ag), silver chloride (AgCl), silver-plated brass (Ms/Ag), silver-plated copper (Cu/Ag), and steel. In an example, naturally non-conductive (or less conductive) electroconductive threads, fibers, yarns, strands, filaments, traces, layers, inks, and/or resins can be made conductive by combining them with material selected from the group consisting of: aluminum (Al), aluminum alloy, brass (Ms), carbon nanotubes, carbon-based material, ceramic particles, copper (Cu), copper alloy, copper-clad aluminum, fluorine rubber, fluorine surfactant, gold (Au), graphene, magnesium, nickel, niobium (Nb), organic solvent, polyaniline, polymer, rubber, silicone, silver (Ag), silver chloride (AgCl), silver-plated brass (Ms/Ag), silver-plated copper (Cu/Ag), and steel. In an example, electroconductive threads, fibers, yarns, strands, filaments, traces, and/or layers can be selected from the group consisting of: conductive core yarn, copper thread coated with polyester, polyester yarn coated with metal, steel fiber yarn, synthetic filament fiber yarn, yarn coated with carbon, yarn coated with copper, and yarn coated with silver.

In an example, an electronically-functional fabric or textile, and/or article of clothing with electromyographic sensors can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, the electroconductive threads, yarns, fibers, strands, channels, and/or traces comprising electromyographic sensors in clothing can have shapes or configurations which are selected from the group consisting of: circular, elliptical, or other conic section; square, rectangular, hexagon, or other polygon; parallel; perpendicular; crisscrossed; nested; concentric; sinusoidal; undulating; zig-zagged; and radial spokes. In an example, an electronically-functional fabric, textile, and/or article of clothing with electromyographic sensors can be created by weaving, knitting, sewing, embroidering, layering, laminating, adhering, melting, fusing, printing, spraying, painting, or pressing electroconductive threads, fibers, yarns, strands, filaments, traces, and/or layers together with non-conductive threads, fibers, yarns, filaments, traces, and/or layers.

In an example, an electronically-functional fabric, textile, and/or article of clothing with electromyographic sensors can be created by printing, spraying, or otherwise depositing electroconductive ink or resin onto an otherwise non-conductive fabric, textile, and/or article of clothing. In an example, an electronically-functional circuit with electromyographic sensors can be created as part of an article of clothing by printing a conductive pattern with electroconductive ink or resin. In an example, an electronically-functional fabric, textile, and/or article of clothing with electromyographic sensors can be created by laminating electro-conductive members onto a non-conductive substrate. In an example, an electronically-functional fabric, textile, and/or article of clothing with electromyographic sensors can be created by embroidering a generally non-conductive fabric or textile member with electro-conductive members. In an example, an electronically-functional circuit with electromyographic sensors can be created for an article of clothing by embroidering a conductive pattern with electroconductive thread.

In an example, an article of electromyographic clothing can be made from one or more elastic, stretchable, and/or tight-fitting materials. In an example, an article of electromyographic clothing or accessory can be made from one or more materials selected from the group consisting of: Acetate, Acrylic, Cotton, Denim, Latex, Linen, Lycra[R], Neoprene, Nylon, Polyester, Rayon, Silk, Spandex, and Wool. In an example, an article of electromyographic clothing can have a uniform elasticity and/or tightness of fit which enables collection of muscle activity data by electromyographic sensors on virtually any body surface location covered by the clothing.

In an example, an article of electromyographic clothing can have one or more selected areas with greater elasticity and/or tighter fit which enable collection of muscle activity data by electromyographic sensors from these one or more selected areas. In an example, the locations of one or more selected areas with greater elasticity and/or tighter fit can be selected in order to optimally measure muscle activity. In an example, the locations of one or more selected areas with greater elasticity and/or tighter fit can be moved longitudinally or laterally along a body surface in order to optimally measure muscle activity. In an example, the elasticity and/or fit of one or more selected areas of an article of electromyographic clothing can be adjusted and/or changed in order to optimally measure muscle activity.

In an example, the locations of one or more selected areas with greater elasticity and/or tighter fit can be selected in order to optimally measure muscle activity by a specific person or during a specific type of physical activity. In an example, the locations of one or more selected areas with greater elasticity and/or tighter fit can be moved longitudinally or laterally along a body surface in order to optimally measure muscle activity by a specific person or during a specific type of physical activity. In an example, the elasticity and/or fit of one or more selected areas of an article of electromyographic clothing can be adjusted and/or changed in order to optimally measure muscle activity by a specific person or during a specific type of physical activity.

In an example, an article of electromyographic clothing can be close-fitting so that one or more electromyographic sensors are in close proximity to a wearer's skin. In an example, an article of electromyographic can be close-fitting so that one or more electromyographic sensors do not shift very much with respect to a wearer's skin when the wearer moves. In an example, an article of electromyographic clothing can have generally uniform closeness of fit on a person's body. In an example, an article of electromyographic clothing can have selected portions with a closer and/or tighter fit in order to better measure electromyographic signals from those selected portions. In an example, an article of electromyographic clothing can have a generally loose fit, but also have one or more selected compressive bands which fit more closely or tightly against the wearer's skin. In an example, one or more compressive bands can be integral parts of an article of electromyographic clothing. In an example, or more compressive bands can be modular and adjustably placed at different locations on an article of electromyographic clothing.

In an example, an article can have a first set of portions of electromyographic clothing with a first level of elasticity, closeness of fit, or tightness and can have a second set of portions of electromyographic clothing with a second level of elasticity, closeness of fit, or tightness, wherein the second level is greater than the first level. In an example, selected areas with a greater elasticity, closeness of fit, or tightness can be permanently located at selected locations in an article of electromyographic clothing. In an example, selected clothing components and/or areas with greater elasticity, closeness of fit, or tightness can be modular. In an example, selected components of electromyographic clothing with greater elasticity, closeness of fit, or tightness can be removably-attached and/or moved to different locations on an article of electromyographic clothing.

In an example, an article of electromyographic clothing can comprise: an article of clothing worn by a person which further comprises; a first set of one or more portions of the clothing with a first level of elasticity; a second set of one or more portions of the clothing with a second level of elasticity, wherein the second level is greater than the first level; and a set of electromyographic sensors wherein these sensors are configured to collect data concerning electromagnetic energy which is generated by muscle tissue and/or nerves which innervate that muscle tissue, wherein these electromyographic sensors are attached to and/or part of the second set of one or more portions of the clothing.

In an example, an article of electromyographic clothing can include one or more circumferential compressive bands with a greater elasticity, closeness of fit, or tightness that the rest of the article, wherein there are one or more electromyographic sensors on these bands. In an example, an article of electromyographic clothing can include one or more such compressive bands on portions of the article which span a person's arm and/or leg. In an example, the locations of one or more compressive bands with respect to a person's arm and/or leg can be adjusted by reversibly attaching one or more compressive bands to different locations on an article of electromyographic clothing.

In an example, an article of electromyographic clothing can include one or more helical and/or spiral members with a greater elasticity, closeness of fit, or tightness that the rest of the article, wherein there are one or more electromyographic sensors on these bands. In an example, an article of electromyographic clothing can include one or more such helical and/or spiral members on portions of the article which span a person's arm and/or leg. In an example, the locations of one or more helical and/or spiral members with respect to a person's arm and/or leg can be adjusted by reversibly attaching (or sliding or rotating) the one or more helical and/or spiral members to different locations on an article of electromyographic clothing.

Let us continue this introduction by providing some more detail concerning electromyographic sensors. The combination of a group of muscle fibers and a motor neuron which innervates that group is called a Motor Unit (MU). Different motor units have different electromagnetic energy signal patterns. An electromyographic sensor generally receives an electromagnetic energy signal which is a combination of electromagnetic energy signals from multiple nearby motor units. In an example, electromagnetic current can be created or altered within an electromyographic sensor by electromagnetic conduction, induction, and/or capacitance. The electromagnetic energy signal received by an electromyographic sensor can be amplified locally before it is transmitted to a data processing unit.

Contracting muscle fibers cause electrical potentials and electromagnetic signals which can be measured from the surface of a person's skin. In an example, an article of electromyographic clothing can incorporate one or more electromyographic sensors which do not penetrate a person's skin. In an example, an electromyographic sensor can be a surface electromyographic (sEMG) sensor. A surface electromyographic sensor measures the combined electromagnetic energy which reaches a person's skin from underlying electrical potentials that travel along one or more nearby contracting muscles. A surface electromyographic (sEMG) sensor will receive stronger EMG signals from nerves and muscles which are closer to the surface of the skin than from deeper nerves and muscles. In an example, an electromyographic sensor can be a capacitive electromyographic (cEMG) sensor.

An electromyographic sensor which is part of an article of electromyographic clothing can comprise one electrode. In an example, an electromyographic sensor can comprise two electrodes. In an example, an electromyographic sensor can be a bipolar sensor with a ground electrode and a sensor electrode. In an example, an electromyographic sensor can comprise multiple electrodes. In an example, two sensor electrodes can be coupled with an amplifier which increases the voltage difference between them. In an example, the output of an amplifier can be sent to an analog-to-digital converter. In an example, an electromyographic sensor can measure changes in electromagnetic energy flow between two electrodes based on one or more parameters selected from the group consisting of: voltage, resistance, impedance, amperage, current, phase, and wave pattern.

In an example, an electromyographic sensor which is part of an article of electromyographic clothing can be selected from the group consisting of: bipolar EMG sensor; capacitive-coupling EMG sensor; circular sensor; conductive electrode EMG sensor; conductive yarn EMG sensor; contactless EMG sensor; copper-coated fiber EMG sensor; electromagnetic impedance sensor; monopolar EMG sensor; non-gelled EMG sensor; non-invasive EMG sensor; silver-coated fiber EMG sensor; square EMG sensor; and surface EMG sensor. In an example, one or more mechanomyography (MMG) sensors can be substituted or added. In an example, one or more sonomyography (SMG) sensors can be substituted or added.

With respect to shape, an electromyographic sensor which is part of an article of electromyographic clothing can have one or more shapes which are selected from the group consisting of: arcuate, circular, circumferential band, circumferential ring, conic section, egg shape, ellipse, elliptical, half circumferential band, half circumferential ring, hexagonal, octagonal, oval, rectangular, rhomboid, rounded rectangle, rounded square, sinusoidal, square, straight, trapezoidal, and triangular.

With respect to size, an electromyographic sensor which is part of an article of electromyographic clothing can cover an area of a person's body which is sufficiently large to record electromagnetic signals from a muscle of interest, but not so large as to have these signals confounded by signals from other muscles. A larger sensor can be more robust for measuring neuromuscular signals from a muscle despite shifts in clothing over a person's skin and despite variation in how clothing fits different people's bodies. In an example, an electromyographic sensor can cover an area in the range of 10 mm to 60 mm. With respect to spacing, electromyographic sensors can be spaced between 1 mm to 30 mm apart. Bipolar electrodes can be approximately 10 mm to 30 mm apart.

With respect to orientation, an electromyographic sensor can be placed on or near a person's skin in an orientation which is substantially perpendicular to the longitudinal axis of a body member on which the sensor is located. In another example, an electromyographic sensor can be placed on or near a person's skin in an orientation which is substantially parallel to the longitudinal axis of a body member on which the sensor is located. In an example, an electromyographic sensor can be placed on or near a person's skin in an orientation which forms an acute angle with respect to the longitudinal axis of a body member on which the sensor is located.

In an example, an electromyographic sensor can be placed on or near a person's skin in an orientation which is aligned with (some or all of) the perimeter and/or circumference of a body member on which the sensor is located. In an example, a series of electromyographic sensors can span longitudinally-sequential cross-sectional perimeters of a body member. In an example, the location of a modular electromyographic sensor can be adjusted by connecting the sensor to different pairs of connectors on an article of electromyographic clothing. In an example, the radial location of a modular electromyographic sensor around the perimeter or circumference of a body member can be adjusted by connecting the sensor to different pairs of connectors.

In an example, an article of electromyographic clothing can comprise an array, grid, mesh, or matrix of multiple electromyographic sensors. In an example, one or more EMG sensors in an array can be capacitive, conductive, inductive, and/or impedance sensors. In an example, one or more EMG sensors in an array can be non-invasive, surface, dry, and/or contactless sensors. In an example, an array, grid, mesh, or matrix of electromyographic sensors which are part of an article of electromyographic clothing can be arranged along perpendicular axes in a fabric or textile from which an article of clothing is made so that the areas between sensors form squares or rectangles. In an example, sensors can be arranged in an array so that the areas between sensors are triangular or hexagonal in shape. In an example, a plurality of electromyographic sensors which are part of an article of electromyographic clothing can form an array, grid, mesh, or matrix comprised of connected circles, ovals, ellipsoids, squares, rhombuses, diamonds, trapezoids, parallelograms, triangles, or hexagons.

In an example, an array, grid, mesh, or matrix of electromyographic sensors which are part of an article of electromyographic clothing can be arranged in a series of perimeter and/or circumferential rings, wherein each ring has a different distance from a joint along the longitudinal axis of a body member. In an example, an array, grid, mesh, or matrix of electromyographic sensors which are part of an article of clothing can be configured in one or more rings (or partial rings) around cross-sections of an article of clothing (or a body member spanned by the article of clothing). In an example, an array, grid, mesh, or matrix of electromyographic sensors on an article of electromyographic clothing can be configured in one or more columns which are parallel to the longitudinal axis of the article of clothing (or a body member spanned by the article of clothing).

In an example, there can be a first array of electromyographic sensors on an article of clothing on the proximal portion of a body member (e.g. upper leg or upper arm) and a second array of electromyographic sensors on an article of clothing on the distal portion of a body member (e.g. lower leg or forearm). In an example, there can be a first array of electromyographic sensors on an article of clothing on the anterior portion of a body member and a second array of electromyographic sensors on an article of clothing on the posterior portion of a body member.

In an example, an array of electromyographic sensors can span a percentage of the perimeter or circumference of a cross-section of a body member such as a leg or arm. In an example, this percentage can be within the range of 10% to 25%. In an example, this percentage can be within the range of 25% to 50%. In an example, this percentage can be within the range of 50% to 75%. In an example, this percentage can be within the range of 75% to 100%.

In an example, an array of electromyographic sensors can comprise circular sensors which are located in pairs. In an example, an array of electromyographic sensors can be pairs of electrodes which are attached to a square or oblong substrate and/or surface. In an example, an array of electromyographic sensors can be in pairs which are separated longitudinally along the longitudinal axes of muscles which activate key body joints.

In an example, an array of electromyographic sensors can comprise rings or bands which each span the circumference and/or perimeter of a person's arm, wrist, hand, leg, ankle, or foot. In an example, an array of electromyographic sensors can comprise half-rings or half-bands which each span half of the circumference a person's arm, wrist, hand, leg, ankle, or foot. In an example, an array of electromyographic sensors can comprise quarter-rings or quarter-bands which each span a quarter of the circumference a person's arm, wrist, hand, leg, ankle, or foot. In an example, an array of electromyographic sensors can each span a portion of the circumference of a person's arm or leg at substantially the mid-section of one or more muscles which move one or more arm or leg joints. In an example, an array of electromyographic sensors can each cross the mid-section of one or more muscles at an acute angle, like a chevron.

In an example, a front half of an array of electromyographic sensors can collect data concerning the activity of one or more muscles which move a joint in a first direction and a back half of an array of electromyographic sensors can collect data concerning the activity of one or more muscles which move a joint in a second direction. In an example, a front half of an array of electromyographic sensors can collect data concerning the activity of one or more muscles which move a joint in extension and a back half of an array of electromyographic sensors can collect data concerning the activity of one or more muscles which move a joint in flexion.

In an example, an article of electromyographic clothing can have an available array of electromyographic sensors, but only a subset of that array is activated in order to measure the muscle of a specific person or muscle activity during a specific sport (or other type of physical activity). In an example, the entire available array of sensors can be activated to collect data during a calibration or test period and this data can then be used to select the subset of sensors which are activated on an ongoing basis. In an example, a master model of an article of electromyographic clothing can have a large and/or dense array of sensors, but a customized article of electromagnetic clothing can be created for a specific person or sport with only a subset of the sensors in the master model. In an example, data collected when a person is wearing the master model is used to identify the subset of sensors which is to be included in a customized article of clothing for that person. In an example, data from a large array of sensors can be used to identify the smaller subset of sensors which can most efficiently collect muscle activity for a specific person or during a specific sport.

In an example, an article of electromyographic clothing can have other types of sensors in addition to electromyographic sensors. In an example, joint multivariate analysis of data from two or more different types of sensors can provide more accurate estimation and/or modeling of muscle activity than data from only one type of sensor. In an example, joint multivariate analysis of data from electromyographic sensors and inertial motion sensors can provide more accurate measurement of muscle activity than data from electromyographic sensors alone. In an example, an article of electromyographic clothing with multiple types of sensors can provide information for other purposes in addition to measurement of muscle activity.

In an example, an article of electromyographic clothing can further comprise one or more of the following: accelerometer, air pressure sensor, airflow sensor, altimeter, barometer, bend sensor, chewing sensor, compass, electrogoniometer, eye tracking sensor, force sensor, gesture recognition sensor, goniometer, gyroscope, inclinometer, inertial sensor, mechanomyography (MMG) sensor, motion sensor, piezoelectric sensor, piezoresistive sensor, pressure sensor, strain gauge, stretch sensor, tilt sensor, torque sensor, variable impedance sensor, variable resistance sensor, and vibration sensor.

In an example, an article of electromyographic clothing can further comprise one or more of the following: ambient light sensor, camera, chromatography sensor, chromatography sensor, fluorescence sensor, infrared sensor, light intensity sensor, mass spectrometry sensor, near-infrared spectroscopy sensor, optical sensor, optoelectronic sensor, oximeter, oximetry sensor, photochemical sensor, photoelectric sensor, photoplethysmography (PPG) sensor, spectral analysis sensor, spectrometry sensor, spectrophotometric sensor, spectroscopic sensor, and ultraviolet light sensor.

In an example, an article of electromyographic clothing can further comprise one or more of the following: bio-impedance sensor, capacitive sensor, electrocardiogram (ECG) sensor, electrochemical sensor, electroencephalography (EEG) sensor, electrogastrography (EGG) sensor, electromagnetic impedance sensor, electrooculography (EOG) sensor, electroporation sensor, galvanic skin response (GSR) sensor, Hall-effect sensor, humidity sensor, hydration sensor, impedance sensor, magnetic field sensor, magnometer, mechanomyography (MMG) sensor, moisture sensor, skin conductance sensor, skin impedance sensor, skin moisture sensor, sonomyography (SMG) sensor, and voltmeter. In an example, an article of electromyographic clothing can further comprise one or more of the following: acoustic sensor, ambient sound sensor, audiometer, breathing monitor, microphone, respiration rate monitor, respiratory function monitor, sound sensor, speech recognition sensor, and ultrasound sensor.

In an example, an article of electromyographic clothing can further comprise one or more of the following: ambient temperature sensor, body temperature sensor, skin temperature sensor, temperature sensor, thermal energy sensor, and thermistor. In an example, an article of electromyographic clothing can further comprise one or more of the following: biochemical sensor, blood glucose monitor, blood oximetry sensor, capnography sensor, chemical sensor, chemiresistor sensor, chemoreceptor sensor, cholesterol sensor, glucometer, glucose sensor, osmolality sensor, pH level sensor, pulse oximeter, and tissue oximetry sensor. In an example, an article of electromyographic clothing can further comprise one or more of the following: ambient air monitor, blood flow monitor, blood pressure sensor, body fat sensor, caloric intake monitor, cardiac function sensor, cardiovascular sensor, flow sensor, heart rate sensor, hemoencephalography (HEG) monitor, microbial sensor, microfluidic sensor, pneumography sensor, pulse sensor, spirometry monitor, and swallowing sensor.

In an example, an article of electromyographic clothing can further comprise one or more of the following: actuator, audio speaker, data processor, data processor, global positioning system (GPS) module, micro electromechanical system (MEMS) actuator, piezoelectric actuator, power source, sound-emitting member, speaker, tactile-sensation-creating member, touch-based human-to-computer textile interface, touchpad, wireless data receiver, and wireless data transmitter.

In an example, an article of electromyographic clothing can have multiple electromyographic sensors in different locations, with different orientations, of different sizes, and having different configurations which enables combined, joint, and/or multivariate measurement of muscle activity. In an example, having different sets of electromyographic sensors spanning the same area of a human body can provide redundant data concerning a selected group of muscles which, in turn, can provide more accurate measurement of their muscle activity than a single set of electromyographic sensors.

In an example, having multiple sets of electromyographic sensors with different locations, orientations, sizes, and configurations can provide an over-determined system of equations for measuring muscle activity and/or estimating joint angles. In an example, having multiple sets of electromyographic sensors with different locations, orientations, sizes, and configurations can reduce measurement variability and error. In an example, having multiple sets of electromyographic sensors with different locations, orientations, sizes, and configurations can control for clothing that shifts or slides with respect to a person's body. In an example, having multiple sets of electromyographic sensors with different locations, orientations, sizes, and configurations can control for changes in clothing proximity, sensor material fatigue, and malfunction of a subset of sensors.

In an example: a first set of electromyographic sensors with a first location, orientation, size, and configuration can provide superior data during a first range of motion, a first number of repeated cycles, a first motion speed, a first clothing location, a first level of clothing elasticity, or a first level of external force or resistance; a second set of electromyographic sensors with a second location, orientation, size, and configuration can provide superior data during a second range of motion, a second number of repeated cycles, a second motion speed, a second clothing location, a second level of clothing elasticity, or a second level of external force or resistance; and combined analysis of data from the first set and the second set can provide more accurate measurement of muscle activity than analysis of data from either set alone.

In an example, a first set of electromyographic sensors provides better measurement of muscle activity during a first condition; a second set of electromyographic sensors provides better measurement of muscle activity during a second condition; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity when an article clothing has a first alignment with a person's body; a second set of electromyographic sensors provides better measurement of muscle activity when the article of clothing has a second alignment with the person's body; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity when a joint is within a first angle range; a second set of electromyographic sensors provides better measurement of muscle activity when the joint is within a second angle range; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity when clothing has a first closeness of fit; a second set of electromyographic sensors provides better measurement of muscle activity when clothing has a second closeness of fit; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity when a joint moves in a first direction; a second set of electromyographic sensors provides better measurement of muscle activity when the joint moves in a second direction; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity during a first duration of motion; a second set of electromyographic sensors provides better measurement of muscle activity during a second duration of motion; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity during a first exertion level; a second set of electromyographic sensors provides better measurement of muscle activity during a second exertion level; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity during a first level of type of environmental interference (such as environmental electromagnetic energy, light, sound, moisture, or movement); a second set of electromyographic sensors provides better measurement of muscle activity during a second level of type of environmental interference; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity during a first type or pattern of motion; a second set of electromyographic sensors provides better measurement of muscle activity during a second type or pattern of motion; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity during a first range of motion; a second set of electromyographic sensors provides better measurement of muscle activity during a second range of motion; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity during a first number of repeated motions; a second set of electromyographic sensors provides better measurement of muscle activity during a second number of repeated motions; combined multivariate analysis of data from both sets of sensors provides more accurate overall measurement of muscle activity than data from either set alone; and an article of clothing includes both sets of sensors.

In an example: a first set of electromyographic sensors provides better measurement of muscle activity at a first muscle movement speed; a second set of electromyographic sensors provides better measurement of muscle activity at a second muscle movement speed; combined multivariate analysis of data from both sets of sensors provides more accurate overall measurement of muscle activity than data from either set alone; and an article of clothing includes both sets of sensors.

In an example, an article of electromyographic clothing can have a second set of wearable sensors in addition to a first set of electromyographic sensors. In an example, the second set of wearable sensors can be inertial motion sensors, such as accelerometers. In an example, the second set of wearable sensors can be bending motion sensors, such as electrogoniometers. In an example, sensors in the second set can be selected from the group consisting of: accelerometer, air pressure sensor, airflow sensor, altimeter, barometer, bend sensor, chewing sensor, compass, electrogoniometer, eye tracking sensor, force sensor, gesture recognition sensor, goniometer, gyroscope, inclinometer, inertial sensor, mechanomyography (MMG) sensor, motion sensor, piezoelectric sensor, piezoresistive sensor, pressure sensor, strain gauge, stretch sensor, tilt sensor, torque sensor, variable impedance sensor, variable resistance sensor, and vibration sensor.

In an example, sensors in the second set can be selected from the group consisting of: ambient light sensor, camera, chromatography sensor, chromatography sensor, fluorescence sensor, infrared sensor, light intensity sensor, mass spectrometry sensor, near-infrared spectroscopy sensor, optical sensor, optoelectronic sensor, oximeter, oximetry sensor, photochemical sensor, photoelectric sensor, photoplethysmography (PPG) sensor, spectral analysis sensor, spectrometry sensor, spectrophotometric sensor, spectroscopic sensor, and ultraviolet light sensor.

In an example, sensors in the second set can be selected from the group consisting of: bioimpedance sensor, electrocardiogram (ECG) sensor, electrochemical sensor, electroencephalography (EEG) sensor, electrogastrography (EGG) sensor, electromagnetic impedance sensor, electrooculography (EOG) sensor, electroporation sensor, galvanic skin response (GSR) sensor, Hall-effect sensor, humidity sensor, hydration sensor, impedance sensor, magnetic field sensor, magnometer, moisture sensor, skin conductance sensor, skin impedance sensor, skin moisture sensor, and voltmeter. In an example, sensors in the second set can be selected from the group consisting of: acoustic sensor, ambient sound sensor, audiometer, breathing monitor, microphone, respiration rate monitor, respiratory function monitor, sound sensor, speech recognition sensor, and ultrasound sensor.

In an example, sensors in the second set can be selected from the group consisting of: ambient temperature sensor, body temperature sensor, skin temperature sensor, temperature sensor, thermal energy sensor, and thermistor. In an example, sensors in the second set can be selected from the group consisting of: biochemical sensor, blood glucose monitor, blood oximetry sensor, capnography sensor, chemical sensor, chemiresistor sensor, chemoreceptor sensor, cholesterol sensor, glucometer, glucose sensor, osmolality sensor, pH level sensor, pulse oximeter, and tissue oximetry sensor. In an example, sensors in the second set can be selected from the group consisting of: ambient air monitor, blood flow monitor, blood pressure sensor, body fat sensor, caloric intake monitor, cardiac function sensor, cardiovascular sensor, flow sensor, heart rate sensor, hemoencephalography (HEG) monitor, microbial sensor, microfluidic sensor, pneumography sensor, pulse sensor, spirometry monitor, and swallowing sensor.

In an example, electromyographic clothing which includes a second set of a different type of wearable sensors (other than electromyographic sensors) can provide redundant data concerning the activity of a selected group of muscles—enabling more accurate measurement of this muscle activity than clothing which uses electromyographic sensors alone. In an example, having two or more sets of different types of sensors can provide: an over-determined system of equations for joint angle estimation; reduced measurement error; reduced measurement variability; a means to control for shifting or sliding of the sensors with respect to a person's body; a means to control for changes in clothing proximity to the body; and a means to control for material fatigue and sensor malfunction.

In an example: a first set of electromyographic sensors can provide superior data during a first range of motion, a first number of repeated cycles, a first motion speed, a first clothing location, a first level of clothing elasticity, or a first level of external force or resistance; a second set of another type of wearable sensors can provide superior data during a second range of motion, a second number of repeated cycles, a second motion speed, a second clothing location, a second level of clothing elasticity, or a second level of external force or resistance; and combined analysis of data from the first set of electromyographic sensors and data from the second set of the other type of sensors can provide more accurate measurement of muscle activity than analysis of data from either type of sensor alone.

In an example, a first set of sensors (comprised of EMG sensors) provides better measurement of muscle activity during a first condition; a second set of sensors (comprised of another type of wearable sensors which are not EMG sensors) provides better measurement of muscle activity during a second condition; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity when an article clothing has a first alignment with a person's body; a second set of sensors (comprised of another type of wearable sensors which are not EMG sensors) provides better measurement of muscle activity when the article of clothing has a second alignment with the person's body; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity when a joint is within a first angle range; a second set of sensors (comprised of another type of wearable sensors which are not EMG sensors) provides better measurement of muscle activity when the joint is within a second angle range; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity when clothing has a first closeness of fit; a second set of sensors (comprised of another type of wearable sensors which are not EMG sensors) provides better measurement of muscle activity when clothing has a second closeness of fit; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity when a joint moves in a first direction; a second set of sensors (comprised of another type of wearable sensors which are not EMG sensors) provides better measurement of muscle activity when the joint moves in a second direction; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first duration of motion; a second set of sensors (comprised of another type of wearable sensors which are not EMG sensors) provides better measurement of muscle activity during a second duration of motion; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first exertion level; a second set of sensors (comprised of another type of wearable sensors which are not EMG sensors) provides better measurement of muscle activity during a second exertion level; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first level of type of environmental interference (such as environmental electromagnetic energy, light, sound, moisture, or movement); a second set of sensors (comprised of another type of wearable sensors which are not EMG sensors) provides better measurement of muscle activity during a second level of type of environmental interference; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first type or pattern of motion; a second set of sensors (comprised of another type of wearable sensors which are not EMG sensors) provides better measurement of muscle activity during a second type or pattern of motion; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first range of motion; a second set of sensors (comprised of another type of wearable sensors which are not EMG sensors) provides better measurement of muscle activity during a second range of motion; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity during a first number of repeated motions; a second set of sensors (comprised of another type of wearable sensors which are not EMG sensors) provides better measurement of muscle activity during a second number of repeated motions; combined multivariate analysis of data from both sets of sensors provides more accurate overall measurement of muscle activity than data from either set alone; and an article of clothing includes both sets of sensors.

In an example: a first set of sensors (comprised of EMG sensors) provides better measurement of muscle activity at a first muscle movement speed; a second set of sensors (comprised of another type of wearable sensors which are not EMG sensors) provides better measurement of muscle activity at a second muscle movement speed; combined multivariate analysis of data from both sets of sensors provides more accurate overall measurement of muscle activity than data from either set alone; and an article of clothing includes both sets of sensors.

In an example, multivariate analysis of muscle activity data collected by multiple sets wearable sensors can take into account (control for) conditions which affect data collection. These conditions can be selected from the group consisting of: amount of skin perspiration, skin temperature, environmental moisture and/or humidity level, ambient temperature, altitude and/or atmospheric pressure, amount of body hair in proximity to a sensor, amount of body fat, wearer age, muscle length, electrode motion and shifting, duration and/or intensity of exercise duration, exercise history, and level of external force and/or resistance.

In an example, an article of electromyographic clothing can be made from an electromagnetically-functional fabric or textile. In an example, an electromagnetically-function fabric or textile can be creating using a plain weave, rib weave, basket weave, twill weave, satin weave, or leno weave. In an example, an electromagnetically-functional fabric or textile can be made by weaving, knitting, braiding, sewing, embroidering, fusing, layering, laminating, printing, or pressing together an array of electroconductive fibers, cables, filaments, strands, threads, traces, wires, or yarns. In an example, electroconductive fibers, cables, filaments, strands, threads, traces, wires, or yarns can be woven, knitted, braided, sewn, embroidered, fused, layered, laminated, printed, or pressed together with non-electroconductive fibers, cables, strands, threads, traces, wires, or yarns. In an example, electroconductive fibers, cables, filaments, strands, threads, traces, wires, or yarns can be embroidered, fused, layered, laminated, printed, pressed, or sprayed onto a layer of non-electroconductive fabric, textile, or other flexible material.

In an example, an electroconductive fiber, cable, filament, strand, thread, trace, wire, or yarn can be created by coating, impregnating, or mixing a non-conductive (or less conductive) material with a conductive (or more conductive) material. In an example, an electroconductive fiber, cable, filament, strand, thread, trace, wire, or yarn can be created using one or more materials selected from the group consisting of: acetate, acrylic, ceramic particles, cotton, denim, elastane, flax, fluorine, latex, linen, Lycra™, neoprene, nylon, organic solvent, polyamide, polyaniline, polyester, polymer, polypyrrole, polyurethane, rayon, rubber, silicon, silicone, silk, spandex, wool, aluminum, aluminum alloy, brass, carbon, carbon nanotubes, copper, copper alloy, gold, graphene, Kevlar™, magnesium, Mylar™, nickel, niobium (Nb), silver, silver alloy, silver epoxy, and steel.

In an example, an electroconductive fiber, cable, filament, strand, thread, trace, wire, or yarn can be substantially straight within an electromagnetically-functional fabric or textile. In an example, an electroconductive fiber, cable, filament, strand, thread, trace, wire, or yarn can have a wave pattern within an electromagnetically-functional fabric or textile. In an example, an electroconductive fiber, cable, filament, strand, thread, trace, wire, or yarn can have a sinusoidal shape. In an example, an electroconductive fiber, cable, filament, strand, thread, trace, wire, or yarn can span a portion of the perimeter or circumference of a body member. In an example, two sets of electroconductive fibers, cables, filaments, strands, threads, traces, wires, or yarns can overlap and/or intersect in a substantially perpendicular manner within an electromagnetically-functional fabric or textile. In an example, a first set of electroconductive fibers, cables, filaments, strands, threads, traces, wires, or yarns and a second set of electroconductive fibers, cables, filaments, strands, threads, traces, wires, or yarns can overlap and/or intersect in a substantially perpendicular manner within an electromagnetically-functional fabric or textile.

In an example, an electronically-functional fabric or textile can be created by printing, silk-screening, spraying, flocking, fusing, adhering, gluing, painting, pressing, or laminating electroconductive ink, resin, fluid, gel, or particles onto a non-conductive (or less conductive) material. In an example, an electromagnetically-functional fabric or textile can be created by printing (two-dimensional or three-dimensional), adhering, depositing, flocking, fusing, gluing, laminating, painting, silk-screening, or spraying fluid, gel, ink, resin, or particles comprising aluminum, aluminum alloy, brass, carbon, carbon nanotubes, copper, copper alloy, gold, graphene, Kevlar™, magnesium, Mylar™, nickel, niobium, silver, silver alloy, silver epoxy, or steel.

In an example, an electronically-functional fabric or textile can be created by etching or cutting an electroconductive layer in a fabric or textile. In an example, an electronically-functional fabric or textile can be created by etching or cutting a non-electroconductive layer between two electroconductive layers in a fabric or textile. In an example, an electronically-functional fabric or textile can be created by etching or cutting using a laser.

In an example, an article of electromyographic clothing can be created using a plain weave, rib weave, basket weave, twill weave, satin weave, or leno weave. In an example, an article of electromyographic clothing can be made by weaving, knitting, braiding, sewing, embroidering, fusing, layering, laminating, printing, or pressing together an array of electroconductive fibers, cables, filaments, strands, threads, traces, wires, or yarns.

In an example, an electroconductive fiber, cable, filament, strand, thread, trace, wire, or yarn can be substantially straight within an article of electromyographic clothing. In an example, an electroconductive fiber, cable, filament, strand, thread, trace, wire, or yarn can have a wave pattern within an article of electromyographic clothing. In an example, an electroconductive fiber, cable, filament, strand, thread, trace, wire, or yarn can have a sinusoidal shape. In an example, an electroconductive fiber, cable, filament, strand, thread, trace, wire, or yarn can span a portion of the perimeter or circumference of a body member. In an example, two sets of electroconductive fibers, cables, filaments, strands, threads, traces, wires, or yarns can overlap and/or intersect in a substantially perpendicular manner within an electromagnetically-functional fabric or textile. In an example, a first set of electroconductive fibers, cables, filaments, strands, threads, traces, wires, or yarns and a second set of electroconductive fibers, cables, filaments, strands, threads, traces, wires, or yarns can overlap and/or intersect in a substantially perpendicular manner within an electromagnetically-functional fabric or textile.

In an example, an article of electromyographic clothing can be created by printing, silk-screening, spraying, flocking, fusing, adhering, gluing, painting, pressing, or laminating electroconductive ink, resin, fluid, gel, or particles onto a non-conductive (or less conductive) material. In an example, an article of electromyographic clothing can be created by printing (two-dimensional or three-dimensional), adhering, depositing, flocking, fusing, gluing, laminating, painting, silk-screening, or spraying fluid, gel, ink, resin, or particles comprising aluminum, aluminum alloy, brass, carbon, carbon nanotubes, copper, copper alloy, gold, graphene, Kevlar™, magnesium, Mylar™, nickel, niobium, silver, silver alloy, silver epoxy, or steel.

In an example, an article of electromyographic clothing can be created by adhering one or more electromyographic sensors to the clothing after the basic form of the clothing has been made. In an example, an article of electromyographic clothing can be created by etching or cutting an electroconductive layer in a fabric or textile. In an example, an article of electromyographic clothing can be created by etching or cutting a non-electroconductive layer between two electroconductive layers in a fabric or textile. In an example, an article of electromyographic clothing can be created by etching or cutting using a laser.

In an example, an article of electromyographic clothing and/or the fabric or textile from which the article is made can be elastic, close-fitting, and/or stretchable so as to bring one or more electromyographic sensors into close proximity with a person's skin. In an example, an article of electromyographic clothing can be made with one or more elastic, close-fitting, and/or stretchable fabrics or textiles selected from the group consisting of: Acetate, Acrylic, Cotton, Denim, Latex, Linen, Lycra[R], Neoprene, Nylon, Polyester, Rayon, Silk, Spandex, and Wool.

In an example, an article of electromyographic clothing can have uniform elasticity, closeness-of-fit, and/or stretchability. In an example, an article of electromyographic can further comprise a first portion with a first level of elasticity, closeness-of-fit, and/or stretchability and a second portion with a second level of elasticity, closeness-of-fit, and/or stretchability. In an example, the second level can be greater than the first level. In an example, electromyographic sensors can be selectively located in (or on) the second portion. In an example, a second portion can be located so as to span a central portion of a selected muscle or muscle group. In an example, a second portion can be located so as to span a central portion of a bone segment between two joints.

In an example, an article of electromyographic clothing can comprise a first portion with a first level of elasticity, closeness-of-fit, and/or stretchability and a second portion with a second level of elasticity, closeness-of-fit, and/or stretchability, wherein the second portion further comprises one or more electromyographic sensors and wherein the location of the second portion can be moved with respect to the first portion. In an example, the second portion can overlap the first portion. In an example, the second portion can fit around the first portion. In an example, the second portion can be reversibly-attached to the first portion. In an example, the location at which the second portion is reversibly attached to the first portion can be moved so as to optimally collect data concerning muscle activity by a specific person or muscle activity during a specific type of physical activity. In an example, the second portion can be attached to the first portion by one or more attachment mechanisms selected from the group consisting of: hook-and-eye (e.g. Velcro™), snap, clip, hook, pin, zipper, insertion into a channel, button, clasp, plug, cord, and tie.

In an example, an article of electromyographic clothing can comprise a first portion with a first level of elasticity, closeness-of-fit, and/or stretchability and a second portion with a second level of elasticity, closeness-of-fit, and/or stretchability, wherein the second portion further comprises one or more electromyographic sensors, and wherein the second portion is closer to a person's skin than the first portion. In an example, the second portion can be interior to the first portion. In an example, the first and second portions can be concentric, with the second portion being inside the first portion. In an example, the first and second portions can be nested, with the second portion being inside the first portion.

In an example, an article of electromyographic clothing can comprise a shirt with a first portion with a first level of elasticity, closeness-of-fit, and/or stretchability and a second portion with a second level of elasticity, closeness-of-fit, and/or stretchability, wherein the second level is greater than the first level, and wherein the second portion can further comprises one or more electromyographic sensors. In an example, the second portion can be located inside the first portion. In an example, the second portion can be located within the sleeve of the first portion. In an example, the second portion can comprise a compressive band which is located within the sleeve of the first portion. In an example, the second portion can be located outside the first portion. In an example, the second portion can be located outside the sleeve of the first portion. In an example, the second portion can comprise a compressive band which is located outside the sleeve of the first portion. In an example, the location of the second portion can be shifted, slide, or otherwise moved with respect to the first portion in order to better collect data concerning muscle activity. In an example, the first and second portions can be in electromagnetic communication with each other.

In an example, an article of electromyographic clothing can comprise a pair of pants or shorts with a first portion with a first level of elasticity, closeness-of-fit, and/or stretchability and a second portion with a second level of elasticity, closeness-of-fit, and/or stretchability, wherein the second level is greater than the first level, and wherein the second portion can further comprises one or more electromyographic sensors. In an example, the second portion can be located inside the first portion. In an example, the second portion can be located within the leg of the first portion. In an example, the second portion can comprise a compressive band which is located within the leg of the first portion. In an example, the second portion can be located outside the first portion. In an example, the second portion can be located outside the leg of the first portion. In an example, the second portion can comprise a compressive band which is located outside the leg of the first portion. In an example, the location of the second portion can be shifted, slide, or otherwise moved with respect to the first portion in order to better collect data concerning muscle activity. In an example, the first and second portions can be in electromagnetic communication with each other.

In an example, an article of electromyographic clothing can comprise a shirt with electromyographic sensors, wherein this shirt has a first configuration with a first level of elasticity, closeness-of-fit, and/or stretchability and a second configuration with a second level of elasticity, closeness-of-fit, and/or stretchability, wherein the second level is greater than the first level. In an example, the shirt can be manually adjusted and/or changed from the first configuration to the second configuration in order to better collect data concerning muscle activity. In an example, the shirt can be automatically adjusted and/or changed from the first configuration to the second configuration in order to better collect data concerning muscle activity.

In an example, an article of electromyographic clothing can comprise a pair of pants or shorts with electromyographic sensors, wherein this pair of pants or shorts has a first configuration with a first level of elasticity, closeness-of-fit, and/or stretchability and a second configuration with a second level of elasticity, closeness-of-fit, and/or stretchability, wherein the second level is greater than the first level. In an example, the shirt can be manually adjusted and/or changed from the first configuration to the second configuration in order to better collect data concerning muscle activity. In an example, the shirt can be automatically adjusted and/or changed from the first configuration to the second configuration in order to better collect data concerning muscle activity.

In an example, adjustment of the elasticity, closeness-of-fit, and/or stretchability of an article of electromyographic clothing (such as a shirt or pair of pants) can be based on analysis of data from electromyographic sensors. In an example, adjustment of the elasticity, closeness-of-fit, and/or stretchability of an article of electromyographic clothing can be based on data from one or more wearable sensors selected from the group consisting of: pressure sensor, strain sensor, and optical sensor. In an example, this adjustment of elasticity, closeness-of-fit, and/or stretchability can be done in an iterative manner. In an example, this adjustment of elasticity, closeness-of-fit, and/or stretchability can be done by inflating a channel or pocket within an article of clothing. In an example, this adjustment of elasticity, closeness-of-fit, and/or stretchability can be done by adjusting a cord, band, or tie on the article of clothing. In an example, this adjustment of elasticity, closeness-of-fit, and/or stretchability can be done automatically by an electromagnetic actuator on (or within) an article of clothing.

In an example, a circumferential array of electromyographic sensors can be embodied in an article of electromyographic clothing whose elasticity, stretchability, closeness-of-fit, and/or compressive pressure can be manually adjusted as it is worn. In an example, a circumferential array of electromyographic sensors can be embodied in an article of electromyographic clothing whose elasticity, stretchability, closeness-of-fit, and/or compressive pressure can be automatically adjusted as it is worn. In an example, the elasticity, stretchability, closeness-of-fit, and/or compress pressure of selected portions of an article of electromyographic clothing can be adjusted by one or more mechanisms selected from the group consisting of: adjusting the position of a hook-and-eye attachment mechanism; inflating of an inflatable member which is part of the article of clothing; rotating a member around which fabric of the article of clothing is wound; shrinking or expanding piezoelectric fibers or strands which are integrated into clothing fabric; and sliding an attachment mechanism along a partially circumferential track which is part of the article of clothing. In an example, a circumferential array of electromyographic sensors can be embodied in an article of clothing made with elastic, stretchable, close-fitting, and/or compressive material with a textile bias which moves electromyographic sensors into close proximity to the surface of a person's body.

In an example, electromagnetic signals from muscles which are received by electromyographic sensors on an article of electromyographic clothing can be monitored. If these electromagnetic signals become weak or inaccurate because the electromyographic sensors are not sufficiently close to a person's body, then one or more circumferential actuators can be contracted so that the article of clothing (and, thus, the sensors) fits closer. In an example, the fit of an article of electromyographic clothing can be adjusted in real time based on data from electromyographic sensors. In an example, an article of electromyographic clothing (or a clothing accessory) can be loose when data collection is not needed, but can be automatically tightened (using one or more actuators) when data collection is needed.

In an example, a circumferential array of electromyographic sensors can be embodied in an article of electromyographic clothing comprising: (a) at least one adjustable circumferential portion of an article of clothing, wherein this portion is configured to span at least 25% of the circumference of the person's arm or leg, wherein this adjustable circumferential portion has a first configuration with a first distance from or first pressure exerted onto the surface of the person's arm or leg, wherein this adjustable circumferential portion has a second configuration with a second distance from or second pressure exerted onto the surface of the person's arm or leg, and wherein the person can change the adjustable circumferential portion from the first configuration to the second configuration while wearing the article of clothing; and (b) at least one electromyographic sensor, wherein this electromyographic sensor is configured to collect data concerning electromagnetic energy from muscle activity of the person's arm or leg, and wherein the distance of this energy sensor from the surface of the person's arm or leg and/or pressure exerted by this energy sensor onto the surface of the person's arm or leg is changed when the adjustable circumferential portion is changed from the first configuration to the second configuration.

In an example, an article of electromyographic clothing can include a mechanism to ensure that the article is worn in a desired position and/or configuration with respect to a person's body and selected muscles therein. In an example, a design or mark on an article of clothing can be configured so that the article of clothing is in a desired position or configuration when the design or mark is aligned with a specific body joint (e.g. aligned with a knee cap or elbow). In an example, an article of electromyographic clothing can be used in combination with an image-analyzing application. In an example, an image of the article being worn by a person can be analyzed in order to determine whether a design or mark on the clothing is in the proper position.

In an example, a hole or opening in an article of clothing can be configured so that the article of clothing is in a desired position or configuration when the hole or opening is over a specific body joint (e.g. over a knee cap or elbow). In an example, a hole or opening in an article of clothing can be configured so that the article of clothing is in a desired position or configuration when a finger or toe, respectively, extends through a hole or opening. In an example, an area on an article of clothing with greater or lesser elasticity can be configured so that the article of clothing is in a desired position or configuration when this area is aligned with a specific body joint.

In an example, an article of electromyographic clothing can be used to adjust the mode and/or energy level of communication via a computer-to-human interface. In an example, this interface can be based on light, sound, or touch. In an example, when data from an electromagnetic muscle activity sensor indicates that a person is very active, then a device can change the mode of a user interface from a touch-based or light-based interface to a sound-based interface that is less likely to be confounded by active motion. In an example, when an electromagnetic muscle activity sensor indicates that a person is very active, then this system can increase the energy level of computer-to-human communication. For example, the system can increase the volume of sound-based communication, increase the brightness of light-based communication, and/or increase the strength of tactile-based communication. In an example, a person can change the mode of a user interface by making a specific hand gesture which is detected by an electromagnetic muscle activity sensor. In an example, a person can increase or decrease the energy level of a user interface by making a first hand gesture or a second hand gesture, respectively, which is detected by an electromagnetic muscle activity sensor.

In an example, an article of electromyographic clothing can be used to modify the filtration of incoming electronic communications and/or notifications in a computer-to-human interface. In an example, communication filtering and/or notification can be modified based on a person's overall level of body motion. In an example, when data from an electromyographic sensor indicates that a person is very active (e.g. probably exercising), then a device can impose more selective criteria which must be met by an electronic communication in order for the person to be immediately notified of that electronic communication. In an example, when data from an electromyographic sensor indicates that a person is very inactive (e.g. probably sleeping), then the system can impose more selective criteria which must be met by an electronic communication in order for the person to be immediately notified of that electronic communication.

In an example, filtering and/or notification functions for incoming electronic communications can be modified based on identification of a particular type or configuration of body motion. In an example, when a person moves their arms or hand into a particular configuration or gesture, then this is identified by the electromagnetic muscle activity sensor and modifies the filtering and/or notification of incoming electronic messages. In an example, when movements of a person's arms indicate that they are probably driving, then this can increase the filtration and/or reduce the notification of incoming electronic communications to automatically improve driving safety. More generally, an article of electromyographic clothing can be part of a physiologically-aware communication notification system wherein the filtration of incoming electronic communications is modified based on a person's body motion, configuration, posture, and/or gestures.

In an example, an article of electromyographic clothing can be used to control the operation of a home appliance or environmental control system. In an example, an article of electromyographic clothing can remotely control the operation of a Heating Ventilation and Air Conditioning (HVAC) system. In an example, an article of electromyographic clothing can remotely control the operation of one or more home appliances and/or devices selected from the group consisting of: air conditioner, ceiling light, coffee maker, dehumidifier, dish washer, door lock, door opener, dryer, fan, freezer, furnace, heat pump, home entertainment center, home robot, hot tub, humidifier, microwave, music player, oven, swimming pool, refrigerator, security camera, robotic guard chicken, sprinkler system, stand-alone lights, television, wall light, washing machine, water heater, water purifier, water softener, window lock, window opener, and wireless network.

In an example, an article of electromyographic clothing can comprise one or more elastic and/or compressive bands holding electromyographic sensors, wherein each band fits snugly around the cross-sectional perimeter of a body member which is covered by the article of clothing. In an example, one or more elastic and/or compressive bands can be an integral part of the primary layer of an article of electromyographic clothing. In an example, one or more elastic and/or compressive bands can be located inside the primary layer of an article of electromyographic clothing. In an example, one or more elastic and/or compressive bands can be located outside the primary layer of an article of electromyographic clothing. In an example, one or more elastic bands with electromyographic sensors can be permanently attached to one or more locations, respectively, on an article of clothing. In an example, the locations of one or more elastic and/or compressive bands can be moved to different locations on an article of clothing.

In an example, a circumferential array of electromyographic sensors can be embodied in an article of electromyographic clothing comprising: (a) an article of clothing worn by a person, wherein this article of clothing further comprises a plurality of attachment mechanisms at different locations on the article of clothing; (b) at least one compressive circumferential member; wherein this compressive circumferential member has a first configuration in which it is removably attached to first attachment mechanism at a first location on the article of clothing, is configured to circumferentially span at least a portion the circumference of a portion of the person's body, and is configured to press the article of clothing toward the surface of this portion of the person's body; wherein this compressive circumferential member has a second configuration in which it is attached to second attachment mechanism at a second location on the article of clothing, is configured to circumferentially span at least a portion the circumference of a portion of the person's body, and is configured to press the article of clothing toward the surface of this portion of the person's body; and (c) at least one electromyographic sensor, wherein this electromyographic sensor is configured to collect data concerning muscle activity from a first location when the at least one compressive circumferential member is in the first configuration and this electromyographic sensor is configured to collected data concerning muscle activity from a second location when the at least one compressive circumferential member is in the second location.

In an example, an article of electromyographic clothing can have one or more holes or openings. In an example, one or more holes on an article of electromyographic clothing can allow an attachable electromyographic sensor to have direct contact with a person's skin when the sensor is attached over the hole. In an example, one or more holes on an article of electromyographic clothing can allow an attachable electromyographic sensor to have direct contact with a person's skin when a compressive band or path containing such a sensor is attached over the hole.

In an example, an article of electromyographic clothing can comprise one or more fabric channels, pockets, or pouches into which one or more electromyographic sensors can be reversibly inserted. In an example, not only can an electromyographic sensor be reversibly inserted into, or removed from, such a fabric channel, pocket, or pouch, but the location of an electromyographic sensor can be further refined by sliding or otherwise moving the sensor within a fabric channel, pocket, or pouch. In an example, a fabric channel can encircle (or partially encircle) an arm or leg and the precise location of an electromagnetic (EMG) sensor around the perimeter of that arm or leg can be adjusted by sliding it to a particular location within the fabric channel. In an example, a fabric channel can longitudinally span (or partially span) an arm or leg and the precise location of an electromagnetic (EMG) sensor along the length of that arm or leg can be adjusted by sliding it to a particular location along the fabric channel.

In an example, placing an electromyographic sensor in a first flexible channel or pathway can provide optimal collection of data concerning muscle activity for a first person with a first body size and/or shape and placing an electromyographic sensor in a second flexible channel or pathway can provide optimal collection of data concerning muscle activity for a second person with a second body size and/or shape. Accordingly, creating an article of clothing with multiple flexible channels or pathways into which one or more electromyographic sensors can be removably inserted can enable optimized and/or customized EMG data collection for a specific person. This can enable more accurate data concerning muscle activity for a specific person. In an example, more-proximal EMG sensor locations can be optimal for a first person and more-distal EMG sensor locations can be optimal for a second person.

In an example, an electromyographic sensor can be inserted into a fabric channel, pocket, or pouch via a hole. In an example, this hole can be closed after an electromyographic sensor has been inserted in order to prevent the sensor from slipping out unintentionally during physical activity. In an example, a hole in a fabric channel can be closed by one or more means selected from the group consisting of: hook-and-eye mechanism, snap, button, zipper, clip, pin, plug, and clasp. In an example, an electromyographic sensor can be attached to a particular location along the longitudinal axis of a fabric channel.

In an example, a fabric channel, pocket, or pouch can be created as part of an article of electromyographic clothing by weaving, knitting, sewing, embroidering, layering, laminating, adhering, melting, fusing, printing, spraying, painting, or pressing. In an example, a fabric channel can be created on (or attached to) the interior surface of an article of clothing which faces toward the wearer's body. In an example, a fabric channel can be created on (or attached to) the exterior surface of an article of clothing which faces away from the wearer's body. In an example, there can be one or more openings, holes, or discontinuities in the interior surface of a fabric channel which enable a sensor within the channel to be in direct contact with the wearer's skin at one or more selected locations. In an example, a user can customize the number, locations, and/or sizes of holes or openings in order to customize an article of clothing for the user and/or for a particular type of physical activity.

In an example, a fabric channel can span the entire perimeter or circumference of a cross-section of a body member spanned by the article of clothing. In an example, a fabric channel can be circular or spiral in shape. In an example, a fabric channel can span a portion of the perimeter or circumference of a cross-section of a body member spanned by the article of clothing. In an example, a fabric channel can be shaped like a section of a circle or other conic section. In an example, a fabric channel can span the anterior portion of the perimeter or circumference of a cross-section of a body member. In an example, a fabric channel can span the posterior portion of the perimeter or circumference of a cross-section of a body member. In an example, a fabric channel can span a lateral portion of the perimeter or circumference of a cross-section of a body member. In an example, a fabric channel can span from 10% to 25%, from 25% to 50%, or from 50% to 75%, or from 75% to 100% of the circumference of a body member.

In an example, an article of electromyographic clothing can comprise: an article of clothing which is configured to span a body member, wherein this article of clothing further comprises a first flexible channel with a longitudinal axis which spans (a portion of) a first cross-sectional perimeter or circumference of the body member and a second flexible channel with a longitudinal axis which spans (a portion of) a second cross-sectional perimeter or circumference of the body member; and an electromyographic sensor for collecting data concerning electromagnetic energy from muscle activity, wherein this sensor is removably inserted into either the first flexible channel or into the second flexible channel depending on whether the first flexible channel or the second flexible channel enables more accurate data collection concerning the muscle activity of a specific person and/or the muscle activity of a specific type of activity.

In an example, an article of electromyographic clothing can comprise one or more (electroconductive) tracks along which one or more electromyographic sensors can be slid in order to find the best measurement locations for collecting data concerning muscle activity. In an example, a track can be circumferential and allow an electromyographic sensor to be slid circumferentially around (a portion of) a person's arm, leg, or torso. In an example, a track can be longitudinal and allow an electromyographic sensor to be slid longitudinally along (a portion of) a person's arm, leg, or torso.

In an example, an article of electromyographic clothing can have an array of electrodes which are integrated into the article of clothing, but only a sub-set of them are activated for use as electromyographic sensors through the use of modular electrical connectors. In an example, a plurality of modular electrical connectors can be removably-attached to electrodes on an article of clothing and only those electrodes which are connected are used to collect muscle activity data. In an example, a modular electrical connector can create an electromagnetic pathway between an electrode in an article of electromyographic clothing and a control unit. In an example, a control unit can further comprise a power source, an amplifier, a data processor, a memory, a data transmitter, a data receiver, and a display screen. In an example, an article of electromyographic clothing can comprise a plurality, array, and/or grid of electromyographic sensors. In an example, not all of these electromyographic sensors collect data concerning muscle activity at a given time—only those which are connected to a control unit by the attachment of a removably-attachable electrical connectors or a series of removably-attachable electrical connectors.

In an example, a circumferential array of electromyographic sensors can be embodied in a method for creating customized electromyographic clothing comprising: creating an image of a specific person's body; using this image to create a virtual kinematic model of this specific person's skeleton, tendons, muscles, and/or nerves; and using this virtual kinematic model to create an article of customized electromyographic clothing for the person, wherein this article of customized electromyographic clothing further comprises one or more electromyographic sensors which collect data the person's neuromuscular activity, and wherein the size, shape, elasticity, and/or electromagnetic sensor configuration of this article of customized electromyographic clothing is customized for this specific person based on the virtual kinematic model.

In an example, an image of a person's body which is used to create a virtual kinematic model can be a moving image, a motion picture, and/or a video. In an example, an image of a person's body which is used to create a virtual kinematic model can be an exterior image of the exterior of a person's clothes and/or the person's skin. In an example, an image of a person's body which is used to create a virtual kinematic model can be an interior image of the person's bones, tendons, muscles, nerves, or other body tissue. In an example, an interior image can be obtained using one of more imaging techniques selected from the group consisting of: x-rays; computerized tomography; magnetic resonance; fluoroscopy; nuclear medicine; and positron emission. In an example, a virtual kinematic model of a specific person's body can include one or more components selected from the group consisting of: bones; joints; tendons; muscles; and efferent nerves.

In an example, one or more characteristics of an article of customized electromyographic clothing can be customized for a specific person based on a virtual kinematic model of that person, wherein these characteristics as selected from the group consisting of: clothing size; clothing shape; clothing elasticity; configuration of electromyographic sensors; configuration of inertial measurement sensors; and configuration of bend sensors. In an example, the position, location, and/or orientation of electromyographic sensors on an article of electromyographic clothing can be customized to optimally collect data concerning muscle activity based on the virtual kinematic model of that person. In an example, the number, proportion, location, size, shape, and orientation of electromyographic sensors and inertial motion sensors on an article of electromyographic clothing can be customized to optimally collect data concerning muscle activity based on the virtual kinematic model of that person.

In an example, a circumferential array of electromyographic sensors can be embodied in a method for creating customized electromyographic clothing comprising: creating images of one or more people playing a selected sport; using these images to create virtual kinematic models of these people's skeletons, tendons, muscles, and/or nerves while playing this selected sport; and using these virtual kinematic models to create at least one article of customized electromyographic clothing for people to wear playing that sport, wherein this article of customized electromyographic clothing further comprises one or more electromyographic sensors which collect data the person's neuromuscular activity, and wherein the size, shape, elasticity, and/or electromagnetic sensor configuration of this article of customized electromyographic clothing is customized for this selected sport based on these virtual kinematic models.

In an example, images of people playing this sport which are used to create virtual kinematic models can be a moving images, motion pictures, and/or videos. In an example, images of people playing this sport which are used to create virtual kinematic models can be exterior images of the exteriors of these people's clothes and/or skin. In an example, images of people's bodies which are used to create a virtual kinematic models can be an interior images of their bones, tendons, muscles, nerves, or other body tissue. In an example, interior images can be obtained using one of more imaging techniques selected from the group consisting of: x-rays; computerized tomography; magnetic resonance; fluoroscopy; nuclear medicine; and positron emission. In an example, virtual kinematic models of people's bodies can include one or more components selected from the group consisting of: bones; joints; tendons; muscles; and efferent nerves.

In an example, one or more characteristics of an article of customized electromyographic clothing can be customized for a selected sport based on virtual kinematic models of people playing that sport, wherein these characteristics as selected from the group consisting of: clothing size; clothing shape; clothing elasticity; configuration of electromyographic sensors; configuration of inertial measurement sensors; and configuration of bend sensors. In an example, the position, location, and/or orientation of electromyographic sensors on an article of electromyographic clothing can be customized to optimally collect data concerning muscle activity based on the virtual kinematic model of that person. In an example, the number, proportion, location, size, shape, and orientation of electromyographic sensors and inertial motion sensors on an article of electromyographic clothing can be customized to optimally collect data concerning muscle activity based on virtual kinematic models of people playing a selected sport.

In an example, a circumferential array of electromyographic sensors can be embodied in a modular system for creating customized electromyographic clothing comprising: (a) a first set of alternative modules for an article of clothing, wherein each module in this first set is configured to be worn on a first portion of a person's body, wherein at least one module in this first set includes at least one electromyographic sensor, and wherein there is variation in the location, orientation, size, shape, number, and/or configuration of electromyographic sensors between different modules in this first set; and (b) a second set of alternative modules for an article of clothing, wherein each module in this second set is configured to be worn on a second portion of a person's body, wherein at least one module in this second set includes at least one electromyographic sensor, wherein there is variation in the location, orientation, size, shape, number, and/or configuration of electromyographic sensors between different modules in this second set, and wherein a first module is selected from the first set, a second module is selected from the second set, and the selected first and second modules are combined to form part (or all) of a single customized article of clothing for collecting data concerning electromagnetic energy from neuromuscular activity by a specific person or during a specific type of physical activity.

In an example, the orientations of electromyographic sensors can vary across different modules within a set. In an example, the number of electromyographic sensors can vary across different modules within a set. In an example, the size or shape of electromyographic sensors can vary across different modules within a set. In an example, the location of electromyographic sensors can vary across different modules within a set. In an example, the type or fit of fabric or textile can vary across different modules within a set. In an example, some modules can be larger in size and other modules can be smaller in size in order to customize an article of clothing for variation in a specific person's body shape. In an example, modules can vary in elasticity and/or stretchability in order to achieve the right fit on a specific person's body shape.

In an example, a system of modular electromyographic clothing can include a removably-attachable electromyographic patch, wherein this electromyographic patch includes one or more electromyographic sensors. In an example, a removably-attachable electromyographic patch can be attached to (and removed from) one or more different locations on an article of electromyographic clothing in order to enable collection of muscle activity data from different locations on a person's body. In an example, a system of modular electromyographic clothing can allow a person to test attachment of a removably-attachable electromyographic patch with electromyographic sensors to different locations in order to find the location from which it optimally measures muscle activity for a particular person or a particular sport. In an example, a removably-attachable electromyographic patch can be attached to electromyographic clothing by one or more mechanisms selected from the group consisting of: hook-and-eye material, insertion into a fabric channel or pocket, snap, clip, clasp, hook, plug, loop, and elastic band.

In an example, the shape of a removably-attachable electromyographic patch can be selected from the group consisting of: square, rectangular, saddle, circular, oval, oblong, rounded square, rounded rectangle, and hexagonal. In an example, a removably-attachable electromyographic patch can be attached to the inside surface of an article of electromyographic clothing. In an example, a removably-attachable electromyographic patch can be attached to the outside surface of an article of electromyographic clothing. In an example, a removably-attachable electromyographic patch can be attached to the outside of an article of electromyographic clothing at a location wherein the clothing has a hole so that the electromyographic patch can nonetheless be in direct contact with a person's skin.

In an example, a removably-attachable electromyographic patch can span a selected percentage of the perimeter of a body member such as an arm or leg. In an example, this percentage can be in the range of 25% to 75%. In an example, an electromyographic patch can be slid along the surface of a body member in order to adjust its location with respect to underlying muscles. In an example, an electromyographic patch can be rotated on the surface of a body member in order to adjust its location with respect to underlying muscles.

In an example, an article of electromyographic clothing can have a total array of electromyographic sensors or electrodes, but only a subset of that array of electromyographic sensors or electrodes is activated at a given time. In an example, this subset of electromyographic sensors can be selected so as to most efficiency collect data concerning muscle activity of a specific person or during a specific type of physical activity. In an example, only activating and using a subset of electromyographic sensors can conserve energy.

In an example, a total array of electromyographic sensors can be activated and used during a calibration and/or testing period. Data from the calibration and/or testing period can be analyzed to determine an efficient subset of sensors to activate on an ongoing basis. In an example, a reduction in the number of activated sensors (from total to subset) can be done automatically by a data processing system. In an example, a reduction in the number of activated sensors (from total to subset) can be done manually by manually disconnecting some sensors from activation. In an example, the number of sensors in an activated subset can be at least 25% less than the number of total sensors. In an example, the number of sensors in an activated subset can be at least 50% less than the number of total sensors.

In an example, a master article of electromyographic clothing can have a first (large) array of electromyographic sensors or electrodes. In an example, a person can wear the master article of electromyographic clothing during a calibration and/or testing period in order to determine a subset array of sensors or electrodes which most efficiently collects data concerning muscle activity of that person (with a desired minimum level of accuracy). In an example, data from this calibration and/or testing period is used to identify this efficient subset array of electromyographic sensors and a customized article of electromyographic clothing with that subset array is created for this person. In an example, the customized article of electromyographic clothing can be created from modular components. In an example, the person only wears the master article during a calibration period and the person wears the customized article with the subset array on an ongoing basis. This can help to achieve a desired level of accuracy of muscle activity measurement while containing cost and conserving energy use. In an example, the number of sensors in the customized article can be at least 25% less than number of sensors in the master article. In an example, the number of sensors in the customized article can be at least 50% less than number of sensors in the master article.

In an example, a circumferential array of electromyographic sensors can be embodied in a method for creating a customized article of electromyographic clothing comprising: creating a master model of an article of clothing with a first plurality of electromyographic sensors which collect data concerning muscle activity; having a person wear this master model while the person performs muscle activity; analyzing data from the master model while the person performs muscle activity in order to identify a second plurality of electromyographic sensors on the master model which are most useful for collecting data concerning the muscle activity of this specific person or muscle activity during a specific type of physical activity, wherein the second plurality is a subset of the first plurality; and creating a customized article of clothing to measure muscle activity with the second plurality of electromyographic sensors to collect data concerning muscle activity of this specific person or muscle activity during the specific type of physical activity. In an example, the number of sensors in the second plurality can be less than 50% of the number of sensors in the first plurality. In an example, the number of sensors in the second plurality can be less than 25% of the number of sensors in the first plurality.

In an example, one or more geometric parameters of electromyographic sensors can be adjusted by a person wearing an article of electromyographic clothing. In an example, these adjustable geometric parameters can be selected from the group consisting of: their distance from the surface of the person's body; the pressure which they exert against the surface of the person's body; their flexibility or elasticity; the angle at which they span the longitudinal axis of a muscle; the longitudinal location at which span the longitudinal axis of a muscle; their longitudinal shape; and their cross-sectional shape.

In an example, an article of electromyographic clothing can further comprise one or more components selected from the group consisting of: amplifier, analog-to-digital converter, battery, bioidentification sensor, camera, central processing unit, chemical sensor, computer-to-human interface, control module, data communication component, data control unit, data processor, data receiver, data transmitter, electric motor, electromagnetic actuator, energy-harvesting power source, eyewear, gesture recognition interface, graphic display, keypad, kinetic energy transducer, memory, microprocessor, myostimulator, optical sensor, piezoelectric actuator, power source, signal amplifier, speaker, spectroscopic sensor, speech recognition component, stepper motor, tactile-sensation-creating member, thermal energy transducer, touch screen, visual display, voice producing interface, voice recognition interface, wireless data receiver, and wireless data transmitter.

In an example, an article of electromyographic clothing can enable payment and commerce functionality in situations wherein conventional payment mechanisms are infeasible or inconvenient. In an example, in a zero-gravity situation (such as that encountered by astronauts) where monetary exchange would be difficult, an article of electromyographic clothing can enable commercial exchanges and banking functions. In an example, an article of electromyographic clothing can comprise an astro teller. In an example, a first payment mechanism can be part of an upper arm device and a second payment mechanism can be part of a lower leg device. In an example, the value of a specific transaction could be correlated to the number of payment mechanisms engaged. In an example, some transactions could cost an arm and a leg.

In an example, an article of electromyographic clothing can further comprise a computer-human interface selected from the group consisting of: alarm, animated display, augmented reality display, button, buzzer or alarm, comparing progress toward meeting muscle activity goals with other people, display screen, display showing which muscles a person is using and/or should use, electrical stimulation of the skin, electronically-functional textile, energy balance display, eye gaze tracker, gesture recognition interface, haptic feedback, image projector, infrared light emitter, keypad, light, light display array or matrix, light emitting diode (LED) array or matrix, liquid crystal display (LCD), MEMS actuator, message filtering and/or notification, microphone, myostimulator, neurostimulator, phone call, playing a tone, playing music, real-time coaching advice, ring tone, sharing data with friends, social network interface, speaker or other sound-emitting member, spectroscopic sensor, speech or voice recognition interface, text message, thermometer, touch pad or screen, vibration, and voice message.

In an example, a circumferential array of electromyographic sensors can be embodied in a device and system for measuring body motion and/or muscle activity comprising: (a) one or more articles of clothing or clothing accessories; (b) a plurality of motion sensors which are attached to and/or integrated into the one or more articles of clothing or clothing accessories, wherein these motion sensors are configured to collect motion data concerning changes in the configurations of a set of body joints; (c) a plurality of electromyographic sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and (d) a data processing unit which analyzes both motion data from both the motion sensors and electromagnetic energy data from the EMG sensors to measure and/or model body motion and/or body muscle activity.

In an example, a circumferential array of electromyographic sensors can be embodied in a device and system for measuring body motion and/or muscle activity comprising: (a) one or more articles of clothing or clothing accessories; (b) a plurality of motion sensors which are attached to and/or integrated into the one or more articles of clothing or clothing accessories, wherein these motion sensors are configured to collect motion data concerning changes in the configurations of a set of body joints; (c) a plurality of electromyographic sensors which are attached to and/or integrated into the one or more articles of clothing or clothing accessories, wherein these EMG sensors are configured to collect electromagnetic energy data concerning the neuromuscular activity of a set of muscles, and wherein muscles in the set of muscles move joints in the set of body joints; and (d) a data transmitting unit which transmits both motion data from the motion sensors and electromagnetic energy data from the EMG sensors to a remote data processing unit which analyzes both motion data from the motion sensors and electromagnetic energy data from the EMG sensors to measure and/or model body motion and/or body muscle activity.

In an example, one or more motion sensors in a plurality of motion sensors can be selected from the group consisting of: accelerometer; conductive fiber motion sensor; electrogoniometer; fluid pressure sensor; gyroscope; inclinometer; inductive transducer; inertial sensor; longitudinal pressure sensor; magnometer; optical bend sensor; piezoelectric fiber; piezoelectric sensor; piezoresistive fiber; piezoresistive sensor; strain gauge, and ultrasonic motion sensor.

In an example, one or more EMG sensors in a plurality of EMG sensors can be selected from the group consisting of: bipolar EMG sensor; capacitive-coupling EMG sensor; circular sensor; conductive electrode EMG sensor; conductive yarn EMG sensor; contactless EMG sensor; copper-coated fiber EMG sensor; electromagnetic impedance sensor; monopolar EMG sensor; non-gelled EMG sensor; non-invasive EMG sensor; silver-coated fiber EMG sensor; square EMG sensor; and surface EMG sensor.

In an example, each EMG sensor can be configured to collect electromagnetic muscle activity from a location selected from the group consisting of: the anterior portion of the deltoideus muscle; the deltoideus medius muscle; the gluteus maximus muscle; the gluteus medius muscle; the lateral head of the triceps brachii muscle; the lateralis of the sastrocnemius muscle; the long head and short head of the biceps femoris muscle; the long head of the triceps brachii muscle; the medialis of the gastrocnemius muscle; the peroneus brevis muscle; the peroneus longus muscle; the posterior portion of the deltoideus muscle; the rectus femoris of the quadriceps femoris muscle; the semitendinosus muscle; the short head and/or long head of the biceps brachii muscle; the soleus muscle; the tensor fasciae latae muscle; the tibialis anterior muscle; the vastus lateralis of the quadriceps femoris muscle; and the vastus medialis of the quadriceps femoris muscle.

In an example, one or more EMG sensors can be configured to collect electromagnetic muscle activity from a plurality of locations selected from the group consisting of: the anterior portion of the deltoideus muscle; the deltoideus medius muscle; the gluteus maximus muscle; the gluteus medius muscle; the lateral head of the triceps brachii muscle; the lateralis of the sastrocnemius muscle; the long head and short head of the biceps femoris muscle; the long head of the triceps brachii muscle; the medialis of the gastrocnemius muscle; the peroneus brevis muscle; the peroneus longus muscle; the posterior portion of the deltoideus muscle; the rectus femoris of the quadriceps femoris muscle; the semitendinosus muscle; the short head and/or long head of the biceps brachii muscle; the soleus muscle; the tensor fasciae latae muscle; the tibialis anterior muscle; the vastus lateralis of the quadriceps femoris muscle; and the vastus medialis of the quadriceps femoris muscle.

In an example, a set of body joints whose motions are tracked can be selected from the group consisting of: knee, elbow, hip, pelvis, shoulder, ankle, foot, toe, wrist, palm, finger, torso, rib cage, spine, neck, and jaw. In an example, an article of clothing can be selected from the group consisting of: shirt, blouse, jacket, pants, dress, shorts, glove, sock, shoe, underwear, belt, and union suit. In an example, an article of clothing can be selected from the group consisting of: shirt, T-shirt, blouse, sweatshirt, sweater, neck tie, collar, cuff, jacket, vest, other upper-body garment, pants, shorts, jeans, slacks, sweatpants, briefs, skirt, other lower-body garment, underwear, underpants, panties, pantyhose, jockstrap, undershirt, bra, brassier, girdle, bathrobe, pajamas, hat, cap, skullcap, headband, hoodie, poncho, other garment with hood, sock, shoe, sneaker, sandal, other footwear, suit, coat, dress, jump suit, one-piece garment, union suit, swimsuit, bikini, other full-body garment, and glove.

In an example, an article of clothing can be made from one or more materials selected from the group consisting of: Acetate, Acrylic, Cotton, Denim, Latex, Linen, Lycra®, Neoprene, Nylon, Polyester, Rayon, Silk, Spandex, and Wool. In an example, an article of clothing can be made from fabric and/or constructed in such a manner that it does not shift with respect to the person's skin when a person moves a body joint. In an example, an article of clothing can be close-fitting so that it does not shift with respect to a person's skin when the person moves a body joint. In an example, an article of clothing can cling to a person's skin so that it does not shift with respect to the person's skin when the person moves a body joint.

In an example, a clothing accessory can be selected from the group consisting of: a flexible adhesive member that is attached to the skin spanning a knee; a flexible adhesive member that is attached to the skin spanning an elbow; a flexible adhesive member that is attached to the skin spanning a shoulder; a flexible adhesive member that is attached to the skin spanning a hip; a flexible adhesive member that is attached to the skin spanning an ankle; and a flexible adhesive member that is attached to the skin spanning the torso and/or waist.

In an example, a clothing accessory can be selected from the group consisting of: a flexible bandage that is attached to the skin spanning a knee; an flexible bandage that is attached to the skin spanning an elbow; a flexible bandage that is attached to the skin spanning a shoulder; a flexible bandage that is attached to the skin spanning a hip; a flexible bandage that is attached to the skin spanning an ankle; and a flexible bandage that is attached to the skin spanning the torso and/or waist.

In an example, a clothing accessory can be selected from the group consisting of: an electronic tattoo that is attached to the skin spanning a knee; an electronic tattoo that is attached to the skin spanning an elbow; an electronic tattoo that is attached to the skin spanning a shoulder; an electronic tattoo that is attached to the skin spanning a hip; an electronic tattoo that is attached to the skin spanning an ankle; and an electronic tattoo that is attached to the skin spanning the torso and/or waist.

In other examples, a clothing accessory can be selected from the group consisting of: wrist band, wrist watch, smart watch, bracelet, bangle, strap, other wrist-worn band, eyewear, eyeglasses, contact lens, virtual reality glasses or visor, augmented reality glasses or visor, monocle, goggles, sunglasses, eye mask, visor, electronically-functional eyewear, necklace, neck chain, neck band, collar, dog tags, pendant, beads, medallion, brooch, pin, button, cuff link, tie clasp, finger ring, artificial finger nail, finger nail attachment, finger tube, head band, hair band, wig, headphones, helmet, ear ring, ear plug, ear bud, hearing aid, ear muff, other ear attachment, respiratory mask, face mask, nasal mask, nose ring, nasal pillow, arm bracelet, bangle, amulet, strap, or band, ankle bracelet, bangle, amulet, strap, or band, artificial tooth, dental implant, dental appliance, dentures, dental bridge, braces, upper palate attachment or insert, tongue ring, band, chain, electronic tattoo, adhesive patch, bandage, belt, waist band, suspenders, chest band, abdominal brace, elbow brace, knee brace, shoulder brace, shoulder pad, ankle brace, pocketbook, purse, key chain, and wallet.

In an example, combined and/or multivariate analysis of both (a) motion data from the motion sensors and (b) electromagnetic energy data from the EMG sensors can enable more accurate measurement and/or modeling of body motion than analysis of data from motion sensors alone. In an example, combined and/or multivariate analysis of both (a) motion data from the motion sensors and (b) electromagnetic energy data from the EMG sensors can enable more accurate measurement and/or modeling of body motion than analysis of electromagnetic energy data from the EMG sensors alone. In an example, combined and/or multivariate analysis of both (a) motion data from the motion sensors and (b) electromagnetic energy data from the EMG sensors can enable more accurate measurement and/or modeling of muscle activity than analysis of data from motion sensors alone. In an example, combined, joint, and/or multivariate analysis of both (a) motion data from the motion sensors and (b) electromagnetic energy data from the EMG sensors can enable more accurate measurement and/or modeling of muscle activity than analysis of electromagnetic energy data from the EMG sensors alone.

In an example, data from EMG sensors can supplement data from motion sensors for more accurate measurement of body motion during key portions of joint range of motion wherein data from motion sensors alone is less accurate. In an example, this can be at extreme positions in the range of motion. In an example, data from EMG sensors can supplement data from motion sensors for more accurate measurement of body motion at key times in joint motion wherein data from motion sensors alone is less accurate. In an example, this can be at the beginning or end of a series of repeated actions. In an example, this can be at the beginning or end of a time of especially-strenuous physical activity. In an example, data from EMG sensors can supplement data from motion sensors for more accurate measurement of body motion during isometric activity wherein pressure is being applied against a motion-resisting external object. In an example, data from EMG sensors can supplement data from motion sensors for more accurate measurement of body motion when the person is being moved by an external device such as a car, elevator, escalator, airplane, etc. In an example, data from EMG sensors can supplement data from motion sensors for more accurate measurement of body motion when an article of clothing fits relatively loosely and/or shifts over the surface of the person's skin when the person moves.

In an example, data from motion sensors can supplement data from EMG sensors for more accurate measurement of muscle activity during key portions of joint range of motion wherein data from EMG sensors alone is less accurate. In an example, this can be at extreme positions in the range of motion. In an example, data from motion sensors can supplement data from EMG sensors for more accurate measurement of muscle activity at key times in joint motion wherein data from EMG sensors alone is less accurate. In an example, this can be at the beginning or end of a series of repeated actions. In an example, this can be at the beginning or end of a time of especially-strenuous physical activity. In an example, data from motion sensors can supplement data from EMG sensors for more accurate measurement of muscle activity during isometric activity wherein pressure is being applied against a motion-resisting external object. In an example, data from motion sensors can supplement data from EMG sensors for more accurate measurement of muscle activity when the person is being moved by an external device such as a car, elevator, escalator, airplane, etc. In an example, data from motion sensors can supplement data from EMG sensors for more accurate measurement of muscle activity when an article of clothing fits relatively loosely and/or shifts over the surface of the person's skin when the person moves.

In an example, a device and system for measuring body motion and/or muscle activity with both EMG sensors and motion sensors can be used to measure, estimate, and/or model changes in body configuration and posture. In an example, a device and system for measuring body motion and/or muscle activity with both EMG sensors and motion sensors can be used for motion capture instead of (or in addition to) a camera-based motion capture system. In an example, a device and system for measuring body motion and/or muscle activity with both EMG sensors and motion sensors can be used as a human-to-computer interface for virtual reality or other applications. In an example, a device and system for measuring body motion and/or muscle activity with both EMG sensors and motion sensors can be used for measuring and improving muscle activity and/or athletic performance. In an example, a device and system for measuring body motion and/or muscle activity with both EMG sensors and motion sensors can be used for injury prevention or rehabilitation. In an example, a device and system for measuring body motion and/or muscle activity with both EMG sensors and motion sensors can be used to measure energy expenditure.

In an example, a device and system for measuring body motion and/or muscle activity can (further) comprise one or more sensors selected from the group consisting of: EMG sensor; bending-based motion sensor; accelerometer; gyroscope; inclinometer; vibration sensor; gesture-recognition interface; goniometer; strain gauge; stretch sensor; pressure sensor; flow sensor; air pressure sensor; altimeter; blood flow monitor; blood pressure monitor; global positioning system (GPS) module; compass; skin conductance sensor; impedance sensor; Hall-effect sensor; electrochemical sensor; electrocardiography (ECG) sensor; electroencephalography (EEG) sensor; electrogastrography (EGG) sensor; electromyography (EMG) sensor; electrooculography (EOG); cardiac function monitor; heart rate monitor; pulmonary function and/or respiratory function monitor; light energy sensor; ambient light sensor; infrared sensor; optical sensor; ultraviolet light sensor; photoplethysmography (PPG) sensor; camera; video recorder; spectroscopic sensor; light-spectrum-analyzing sensor; near-infrared, infrared, ultraviolet, or white light spectroscopy sensor; mass spectrometry sensor; Raman spectroscopy sensor; sound sensor; microphone; speech and/or voice recognition interface; chewing and/or swallowing monitor; ultrasound sensor; thermal energy sensor; skin temperature sensor; blood glucose monitor; blood oximeter; body fat sensor; caloric expenditure monitor; caloric intake monitor; glucose monitor; humidity sensor; and pH level sensor.

In an example, a device and system for measuring body motion and/or muscle activity can (further) comprise a human-to-computer interface. This human-to-computer interface can comprise one or more members selected from the group consisting of: buttons, knobs, dials, or keys; display screen; gesture-recognition interface; microphone; physical keypad or keyboard; virtual keypad or keyboard; speech or voice recognition interface; touch screen; EMG-recognition interface; and EEG-recognition interface.

In an example, a device and system for measuring body motion and/or muscle activity can (further) comprise a computer-to-human interface. In an example, this computer-to-human interface can provide feedback to the person concerning their body motion and/or muscle activity. This computer-to-human interface can comprise one or more members selected from the group consisting of: a display screen; a speaker or other sound-emitting member; a myostimulating member; a neurostimulating member; a speech or voice recognition interface; a synthesized voice; a vibrating or other tactile sensation creating member; MEMS actuator; an electromagnetic energy emitter; an infrared light projector; an LED or LED array; and an image projector.

I claim:

1. A circumferential array of electromyographic sensors comprising:
a plurality of circumferential rings of electromyographic sensors which are configured to encircle a selected body member of a person; wherein the selected body member is selected from the group consisting of the person's arm, wrist, hand, finger, leg, ankle, or foot; wherein electromyographic sensors in a ring of electromyographic sensors are at different polar coordinate locations around a circumference of the selected body member; and wherein distances between the electromyographic sensors are adjusted by an electromagnetic actuator, an inflatable chamber or pneumatic member, a hydraulic mechanism, or an adjustable spring; and
a plurality of columns of electromyographic sensors which are configured to be substantially parallel to a longitudinal axis of the selected body member.

2. The circumferential array in claim 1 wherein the polar coordinate locations of electromyographic sensors are evenly spaced around the circumference of the selected body member.

3. The circumferential array in claim 1 wherein the circumferential array is incorporated into an arm band, bangle, or bracelet.

4. The circumferential array in claim 1 wherein the circumferential array is incorporated into a wrist band.

5. The circumferential array in claim 1 wherein the circumferential array is incorporated into a watch strap.

6. The circumferential array in claim 1 wherein the circumferential array is incorporated into the cuff or sleeve of an article of clothing.

7. The circumferential array in claim 1 wherein different sensing roles are assigned to different electromyographic sensors around the circumference of the selected body member in order to correct for physical shifting or rotation of these electromyographic sensors around the selected body member.

8. The circumferential array in claim 1 wherein a ring of electromyographic sensors spans in the range of 50% to 75% of the circumference of a cross-section of the selected body member.

9. The circumferential array in claim 1 wherein a ring of electromyographic sensors spans in the range of 75% to 100% of the circumference of a cross-section of the selected body member.

10. A circumferential array of electromyographic sensors comprising:
- at least three circumferential rings of electromyographic sensors which are configured to encircle a selected body member of a person; wherein the selected body member is selected from the group consisting of the person's arm, wrist, hand, finger, leg, ankle, or foot; wherein electromyographic sensors in a ring of electromyographic sensors are at different polar coordinate locations around a circumference of the selected body member; and wherein the electromyographic sensors are configured to be compelled radially inward toward the body member by an electromagnetic actuator, an inflatable chamber or pneumatic member, a hydraulic mechanism, or an adjustable spring; and
- at least three of columns of electromyographic sensors which are configured to be substantially parallel to a longitudinal axis of the selected body member.

11. The circumferential array in claim 10 wherein the polar coordinate locations of electromyographic sensors are evenly spaced around the circumference of the selected body member.

12. The circumferential array in claim 10 wherein the circumferential array is incorporated into an arm band, bangle, or bracelet.

13. The circumferential array in claim 10 wherein the circumferential array is incorporated into a wrist band or watch strap.

14. The circumferential array in claim 10 wherein the circumferential array is incorporated into the cuff or sleeve of an article of clothing.

15. The circumferential array in claim 10 wherein different sensing roles are assigned to different electromyographic sensors around the circumference of the selected body member in order to correct for physical shifting or rotation of these electromyographic sensors around the selected body member.

16. The circumferential array in claim 10 wherein a ring of electromyographic sensors spans in the range of 50% to 75% of the circumference of a cross-section of the selected body member.

17. The circumferential array in claim 10 wherein a ring of electromyographic sensors spans in the range of 75% to 100% of the circumference of a cross-section of the selected body member.

* * * * *